(12) United States Patent
Kim et al.

(10) Patent No.: US 9,131,722 B2
(45) Date of Patent: Sep. 15, 2015

(54) **COMPOSITION COMPRISING THE EXTRACT OF *ACTINIDIA ARGUTA* AND RELATED SPECIES FOR THE PREVENTION AND TREATMENT OF ALLERGIC DISEASE AND NON-ALLERGIC INFLAMMATORY DISEASE**

(75) Inventors: Bong Cheol Kim, Gwacheon-si (KR); Mi Rim Jin, Seoul (KR); Eun Jin Park, Seoul (KR); Hyung Jin Jung, Seoul (KR); Sung Seup Shin, Seoul (KR); Jin Hwan Oh, Suwon-si (KR); Hwa Jun Lee, Seoul (KR); Sun Young Kim, Seoul (KR); Hyang Jeon, Seoul (KR)

(73) Assignee: VIROMED CO., LTD., Seoul (KR)

( * ) Notice: Subject to any disclaimer, the term of this patent is extended or adjusted under 35 U.S.C. 154(b) by 1086 days.

(21) Appl. No.: 10/646,145

(22) Filed: Aug. 22, 2003

(65) Prior Publication Data
US 2004/0037909 A1 Feb. 26, 2004

Related U.S. Application Data

(60) Provisional application No. 60/405,295, filed on Aug. 23, 2002.

(51) Int. Cl.
  *A01N 65/00* (2009.01)
  *A61K 36/00* (2006.01)
  *A23L 1/30* (2006.01)
  *A61K 36/185* (2006.01)

(52) U.S. Cl.
  CPC ............. *A23L 1/3002* (2013.01); *A61K 36/185* (2013.01); *A23V 2002/00* (2013.01)

(58) Field of Classification Search
  CPC .................................................... A23L 1/3002
  USPC ...................................................... 424/777
  See application file for complete search history.

(56) References Cited

U.S. PATENT DOCUMENTS

| | | | |
|---|---|---|---|
| 3,808,312 A | | 4/1974 | Goulding et al. |
| 4,444,780 A | | 4/1984 | Capetola et al. |
| 5,177,060 A | * | 1/1993 | Wei ................................. 514/15 |
| 5,382,430 A | | 1/1995 | Soma et al. |
| 5,466,841 A | | 11/1995 | Horrobin et al. |
| 5,665,413 A | | 9/1997 | Rossiter |
| 6,197,524 B1 | * | 3/2001 | Romagnani ..................... 435/7.1 |
| 6,369,091 B1 | | 4/2002 | Sircar et al. |
| 6,495,171 B2 | | 12/2002 | Iwase et al. |
| 6,630,163 B1 | * | 10/2003 | Murad ........................... 424/464 |
| 6,863,907 B2 | * | 3/2005 | Kotani et al. ................. 424/771 |
| 2001/0031285 A1 | | 10/2001 | Iwase et al. |
| 2002/0006410 A1 | * | 1/2002 | Lukacs et al. .............. 424/184.1 |
| 2002/0041885 A1 | | 4/2002 | Oomori et al. |
| 2002/0054923 A1 | | 5/2002 | Suzuki et al. |
| 2003/0131370 A1 | | 7/2003 | Allen et al. |
| 2003/0170322 A1 | | 9/2003 | Kayane et al. |
| 2004/0037909 A1 | | 2/2004 | Kim et al. |
| 2007/0122508 A1 | | 5/2007 | Kim et al. |
| 2010/0111927 A1 | | 5/2010 | Kim et al. |

FOREIGN PATENT DOCUMENTS

| | | | |
|---|---|---|---|
| CN | 1107308 A | * | 8/1995 |
| DE | 197 58 090 A1 | | 6/1999 |
| DE | 19758090 | | 6/1999 |
| DE | 19758090 A1 | * | 6/1999 |
| JP | 361140510 A | * | 6/1986 |
| JP | 62-146581 | | 6/1987 |
| JP | 62-146581 A | | 6/1987 |
| JP | 2-202808 | | 8/1990 |
| JP | 2-202808 A | | 8/1990 |
| JP | 02202808 A | * | 8/1990 |
| JP | 7-61915 | | 3/1995 |
| JP | 7-61915 A | | 3/1995 |
| JP | 7-313071 A | | 12/1995 |
| JP | 2001-206836 A | | 7/2001 |
| JP | 2001-220344 | | 8/2001 |
| JP | 2001-220344 A | | 8/2001 |
| JP | 2002-145754 | | 5/2002 |
| JP | 2002-145754 A | | 5/2002 |

(Continued)

OTHER PUBLICATIONS

Wuthrich (Serum IgE in atopic dermatitis; Clinical & Experimental Allergy vol. 8 Issue 3, pp. 241-248).*
Lee et al. (Oral Administration of IL-12 Suppresses Anaphylactic Reactions in a Murine Model of Peanut Hypersensitivity Clinical Immunology vol. 101, No. 2, November, pp. 220-228, 2001).*
Peat, The Epidemiology of Asthma, 1996, p. 11.*
Yudoh et al. (Reduced expression of the regulatory CD4+ T cell subset is related to Th1/Th2 balance and disease severity in rheumatoid arthritis. Arthritis & Rheumatism vol. 43, Issue 3, pp. 617-627, Mar. 2000).*
Myers et al. (The genetic ablation of cyclooxygenase 2 prevents the development of autoimmune arthritis. Arthritis & Rheumatism vol. 43, Issue 12, pp. 2687-2693, Dec. 2000).*
Hunder et al. (Immunoglobulin E (IgE) levels in serum and synovial fluid in rheumatoid arthritis Arthritis & Rheumatism vol. 17, Issue 6, pp. 955-963, Nov./Dec. 1974).*
Permin et al. (Possible Role of Histamine in Rheumatoid Arthritis. Allergy vol. 36, Issue 6, pp. 435-436, Aug. 1981).*

(Continued)

*Primary Examiner* — Layla Soroush
(74) *Attorney, Agent, or Firm* — Judy M. Mohr; McDermott Will & Emery LLP

(57) ABSTRACT

The present invention provides a pharmaceutical composition comprising the extract of hardy kiwifruit as an active ingredient in an effective amount to treat and prevent allergic disease and non-allergic inflammatory disease by reducing inflammation action, by inhibiting histamine release from mast cell, and by increasing the level of Th1 cytokines, IgG2a in serum and reducing the level of Th2 cytokines and IgE in serum. The present invention also provides a use of above extract for the preparation of pharmaceutical composition. The present invention also provides a health food or food additives, a cosmetic composition, a feed or feed additives comprising above extract for prevention or alleviation of allergic disease and non-allergic inflammatory disease by reducing inflammation action, by inhibiting histamine release from mast cell, and by increasing the level of Th1 cytokines, IgG2a in serum, and reducing the level of Th2 cytokines and IgE in serum.

12 Claims, 5 Drawing Sheets

(56) References Cited

FOREIGN PATENT DOCUMENTS

| | | |
|---|---|---|
| JP | 2002-275079 | 9/2002 |
| JP | 2002-275079 A | 9/2002 |
| JP | 2003-61615 | 3/2003 |
| JP | 2003-61615 A | 3/2003 |
| JP | 2003-171294 A | 6/2003 |
| KR | 1994-0001893 A | 2/1994 |
| KR | 1996-004025 A | 3/1996 |
| KR | 2001-0018160 A | 3/2001 |
| KR | 2001-0096881 | 11/2001 |
| KR | 2001-0096881 A | 11/2001 |
| KR | 10-2007-0007837 A | 1/2007 |
| RU | 2 112 524 C1 | 6/1998 |
| WO | WO 0151077 A1 * | 7/2001 |
| WO | WO 01/70259 A | 9/2001 |
| WO | WO 01/70259 A1 | 9/2001 |
| WO | WO 02/069992 A1 | 9/2002 |
| WO | WO 03/103415 A1 | 12/2003 |
| WO | WO 2005/094862 A1 | 10/2005 |

OTHER PUBLICATIONS

McGonagle et al. (The relationship between synovitis and bone changes in early untreated rheumatoid arthritis: A controlled magnetic resonance imaging study. Arthritis & Rheumatism vol. 42, Issue 8, pp. 1706-1711, Aug. 1999).*

Mitsuhashi (Medicinal Plants of the Ainu. Economic Botany 30: 209-217. Jul.-Sep. 1976).*

Zhang et al. (Time Trends of Th1 and Th2 Cytokines in Induced Sputum of Asthmatic Subjects During Acute Upper Respiratory Viral Infections. Arch Bronconeumol. 2010;46:459-65—vol. 46 No. 09).*

Hou et al. (Investigation of Immunopharmacological Activity of Changbai Mountain Actinidia arguta Stem Polysaccharide. China Journal of Chinese Materia Medica. 1995-01).*

Ansel et al. (Pharmaceutical Dosage Forms and Drug Delivery Systems. 1995).*

Viallard et al. (Th1 (IL-2, interferon-gamma (IFN-γ)) and Th2 (IL-10, IL-4) cytokine production by peripheral blood mononuclear cells (PBMC) from patients with systemic lupus erythematosus (SLE). Clinical & Experimental Immunology. vol. 115, Issue 1, pp. 189-195, Jan. 1999).*

Rosemary F. Webby, A Flavonol Triglycoside From *Actinidia arguta* Var. *giraldii*, Phytochemistry, vol. 30, No. 7, pp. 2443-2444, 1991, Great Britain.

Francesco Forastiere, et al., Consumption of fresh fruit rich in vitamin C and wheezing symptoms in children, Thorax 2000, 55:283-288.

Yuko Yoshizawa, et al., Antiproliferative Effects of Small Fruit Juices on Several Cancer Cell Lines, Anticancer Research 20: 4285-4290 (2000).

Ben H. Collins, et al., Kiwifruit Protects Against Oxidative DNA Damage in Human Cells and In Vitro, Nutrition and Cancer, 39(1), 148-153, Lawrence Erlbaum Associates, Inc., 2001.

Noboru Motohashi, et al., Cancer prevention and therapy with Kiwifruit in Chinese folklore medicine: a study of kiwifruit extracts, Journal of Ethnopharmacology 81 (2002) 357.

Hexiang Wang, et al., Isolation of an antifungal thaumatin-like protein from kiwi fruits, Phytochemistry 61 (2002) 1-6.

Yoo Kyung Kim, et al., Anti-Inflamation Activity of *Actinidia polygama*, Arch Pharm Res, vol. 26, No. 12, 1061-1066, 2003.

Matsumoto Osamu, et al., Vinyl Chroride-Based Resin Composition, Patent Abstracts of Japan, Publ. No. 02214754 A, Aug. 27, 1990, Japanese Patent Office.

Jun Ichi Udagawa, Method of Preparing Kiwifruit Liquid, Laid-open Patent Application Gazette (A), Sho 61-140510, Publication date: Jun. 27, 1986, Japan Patent Office.

Fumihide Takano, et al., Protective effect of (+)-catechin against 5-fluorouracil-induced myelosuppression in mice, Toxicology 201 (2004) 133-142.

Huei Lee, et al., Antimutagenic activity of extracts from anticancer drugs in Chinese medicine, Mutation Research, 204 (1988) 229-234.

Joon Ih Whang, et al., Phytochemical Constituents of *Actinidia arguta*, Kor. J. Pharmacogn., 31(3) : 357-363 (2000).

Whang, J.I., et al., "Phytochemical Constituents of *Actinidia arguta*," Kor. J. Pharmacogn. 31:357-363, Korean Society of Pharmacognosy (2000).

Motohashi, N., "Medicinal Uses of the Kiwifruit Family (*Actinidia*)," West Australian Nut and Tree Crops Association 16:48-59, West Australian Nut and Tree Crops Association, Australia (1991).

English language Abstract of Chinese Patent Application No. CN 1107308 A, espacenet DB, (1995).

English language Abstract of Korean Patent Publication No. KR 2001-0096881, espacenet DB, (2001).

Kimata, M. et al., "Effects of Luteolin and Other Flavonoids on IgE-Mediated Allergic Reactions," Planta. Medica. 66:25-29, Georg Thieme Verlag Stuttgart, New York (2000).

Lugasi, A. et al., "Flavonoid Aglycons in Foods of Plant Origin II Fresh and Dried Fruits," Acta. Alimentaria 31:63-71, Akadémiai Kiadó, Budapest (Feb. 2002).

Cheong, H. et al., "Studies of Structure Activity Relationship of Flavonoids for the Anti-allergic Actions," Arch. Pharm. Res. 21:478-480, Pharmaceutical Society of Korea, Korea (1998).

Abbas, A.K., et al., "Functional diversity of helper T lymphocytes," Nature 383(6603):787-93, Nature Publishing Group, England (1996).

Adcock, I.M., "Glucocorticoid-regulated transcription factors," Pulm. Pharmacol. Ther. 14(3):211-9, Academic Press, England (2001).

Allam, J.P., et al., "Characterization of dendritic cells from human oral mucosa: a new Langerhans' cell type with high constitutive FcεRI expression," J Allergy Clin. Immunol. 112(1):141-8, Mosby, United States (2003).

Cheong, H., et al., "Studies of Structure Activity Relationship of flavonoids for the anti-allergic actions," Arch. Pharm. Res. 21:478-80, Pharmaceutical Society of Korea, Korea (1998).

Coffman, R.L. and Carty, J., "A T cell activity that enhances polyclonal IgE production and its inhibition by interferon-γ," J Immunol. 136:949-54, American Association of Immunologists (1986).

Collins, B.H., et al., "Kiwifruit protects against oxidative DNA damage in human cells and in vitro," Nutrition and Cancer 39:148-53, Lawrence Erlbaum Associates, Inc. (2001).

Erb, K.J., "Atopic disorders: a default pathway in the absence of infection?," Immunol. Today, 20:317-22, Elsevier Science Ltd., England (1999).

Fahy, J.V., et al., "The effect of an anti-IgE monoclonal antibody on the early- and late-phase responses to allergen inhalation in asthmatic subjects," Am. J Respir. Crit. Care Med. 155:1828-34, American Thoracic Society, United States (1997).

Forastiere, F., et al., "Consumption of fresh fruit rich in vitamin C and wheezing symptoms in children," Thorax 55:283-8, British Medical Assn., England (2000).

Gavett, S.H., et al., "Interleukin 12 inhibits antigen-induced airway hyperresponsiveness, inflammation, and Th2 cytokine expression in mice," J. Exp. Med. 182(5):1527-36, Rockefeller University Press, United States (1995).

Gerth, A.J., et al., "T-bet regulates T-independent IgG2a class switching," Int. Immunol. 15(8): 937-44, Oxford University Press, England (Aug. 2003).

Grünig, G., et al., "Requirement for IL-13 independently of IL-4 in experimental asthma," Science 282:2261-63, American Assn. for the Advancement of Science, United States (1998).

Harborne J.B., "Methods of plant analysis" in Phytochemical Methods: A guide to modern techniques of plant analysis, $3^{rd}$ edition, Chapman & Hall, London, UK, pp. 6-7 (1998).

Hirano, T., et al., "An improved method for the detection of IgE antibody of defined specificity by ELISA using rat monoclonal anti-IgE antibody," J. Immunol. Methods 119(1):145-50, Elsevier, Netherlands (1989).

Hofstra, C.L., et al., "Prevention of Th2-like cell responses coadministration of IL-12 and IL-18 is associated with inhibition of antigen-induced airway hyperresponsiveness, eosinophilia, and serum IgE levels," J. Immunol. 161(9):5054-60, American Association of immunologists, United States (1998).

(56) References Cited

OTHER PUBLICATIONS

Kaminishi, K., et al., "Flow cytometric analysis of IL-4, IL-13 and IFN-gamma expression in peripheral blood mononuclear cells and detection of circulating IL-13 in patients with atopic dermatitis provide evidence for the involvement of type 2 cytokines in the disease," *J. Dermatol. Sci.* 29(1):19-25, Elsevier, Netherlands (May 2002).

Kato, Y., et al., "Effect of an orally active Th1/Th2 balance modulator, M50367, on IgE production, eosinophilia, and airway hyperresponsiveness in mice," *J. Immunol.* 162(12):7470-9, American Association of Immunologists, United States (1999).

Kiani, A., et al., "Regulation of interferon-gamma gene expression by nuclear factor of activated T cells," *Blood* 98(5): 1480-8, American Hematology, United States (2001).

Kim, H.-M., et al., "Inhibitory effect on immunoglobulin E oroduction in vivo and in vitro by *Siegesbeckia glabrescens*," *Phytother. Res.* 15:572-6, John Wiley & Sons, Ltd., England (2001).

Kim, Y.K., et al., "Anti-inflammation activity of *Actinidia polygama*," *Arch. Pharm. Res.* 26:1061-1066, Pharmaceutical Society of Korea, Korea (Dec. 2003).

Kimata, M. et al., "Effects of luteolin and other flavonoids on IgE-mediated allergic reactions," *Planta. Medica.* 66:25-29, Georg Thieme Verlag Stuttgart, United States (2000).

Konishi, H., et al., "IL-18 contributes to the spontaneous development of atopic dermatitis-like inflammatory skin lesion independently of IgE/stat6 under specific pathogen-free conditions," *Proc. Natl. Acad. Sci. USA* 99(17):11340-5, National Academy of Sciences, United States (Aug. 2002).

Kotani, M., et al., "Persimmon leaf extract and astragalin inhibit development of dermatitis and IgE elevation in NC/Nga mice," *J. Allergy Clin. Immunol.* 106(1 Pt. 1):159-66, Mosby, United States (2000).

Kuchroo, V.K., et al., "B7-1 and B7-2 co-stimulatory molecules activate differentially the Th1/Th2 developmental pathways: application to autoimmune disease therapy," *Cell* 80(5):707-18, Cell Press, United States (1995).

Lee, H.J. et al., "GATA-3 induces T helper cell type 2 (Th2) cytokine expression and chromatin remodeling in committed Th1 cells," *J. Exp. Med.* 192(1):105-15, Rockefeller University Press, United States (2000).

Lee, H. and Lin, J-Y., "Antimutagenic activity of extracts from anticancer drugs in Chinese medicine," *Mutation Research* 204:229-34, Elsevier Science Publishers B.V., The Netherlands (1988).

Leung, D.Y., "Atopic dermatitis: immunobiology and treatment with immune modulators," *Clin. Exp. Immunol.* 107(Suppl 1):25-30, Blackwell Scientific Publications, England (1997).

Leung, D.Y., et al., "Thymopentin therapy reduces the clinical severity of atopic dermatitis," *J. Allergy Clin. Immunol.* 85(5):927-33, Mosby, United States (1990).

Lighvani, A.A., et al., "T-bet is rapidly induced by interferon-gamma in lymphoid and myeloid cells," *Proc. Natl. Acad. Sci. USA* 98(26):15137-42, National Academy of Sciences, United States (2001).

Lugasi, A., et al., "Flavonoid Aglycons in Foods of Plant Origin II Fresh and Dried Fruits," *Acta. Alimentaria* 31:63-71, Akadémiai Kiadó, Budapest (Feb. 2002).

Ma, W., et al., "CCR3 is essential for skin eosinophilia and airway hyperresponsiveness in a murine model of allergic skin inflammation." *J. Clin. Invest.* 109(5): 621-8, American Society for Clinical Investigation, United States (Mar. 2002).

Maggi, E., "The Th1/Th2 paradigm in allergy," *Immunotechnology* 3:233-44, Elsevier Science Ltd., The Netherlands (1998).

Matsuda, H., et al., "Development of atopic dermatitis-like skin lesion with IgE hyperproduction in NC/Nga mice," *Int. Immunol.* 9(3):461-6, Oxford University Press, England (1997).

Motohashi, N., et al., "Cancer prevention and therapy with Kiwifruit in Chinese folklore medicine: a study of kiwifruit extracts," *Journal of Ethnopharmacology* 81:357-64, Elsevier Sequoia, Ireland (Aug. 2002).

Nakatani, T., et al., "CCR4 memory CD4+ lymphocytes are increased in peripheral blood and lesional skin from patients with atopic dermatitis," *J. Allergy Clin. Immunol.* 107(2):353-8, Mosby, United States (2001).

O'Byrne, P.M., et al., "Antileukotrienes in the treatment of asthma," *Ann. Intern. Med.* 127(6):472-80, American College of Physicians—American Society of Internal Medicine, United States (1997).

Oku, H. and Ishiguro, K., "Antipruritic and antidermatitic effect of extract and compounds of *Impatiens balsamina* L. in atopic dermatitis model NC mice," *Phytother. Res.* 15(6):506-10, Wiley, England (2001).

Pawankar, R., "Mast cells as orchestrators of the allergic reaction: the IgE-IgE receptor mast cell network," *Curr. Opin. Allergy Clin. Immunol.* 1(1):3-6, Lippincott Williams & Wilkins, United States (2001).

Rothenberg, M.E., "Eosinophilia," *N. Engl. J. Med.* 338:1592-600, Massachusetts Medical Society, United States (1998).

Schiller, J.T., "Papillomavirus-like particle vaccines for cervical cancer" *Mol. Med. Today* 5(5):209-15, Elsevier Trends Journals, England (1999).

Shibata, Y., et al., "Oral administration of chitin down-regulates serum IgE levels and lung eosinophilia in the allergic mouse," *J. Immunol.* 164(3):1314-21, American Association of Immunologists, United States (2000).

Spergel, J.M., et al., "Roles of Th1 and Th2 cytokines in a murine model of allergic dermatitis," *J. Clin. Invest.* 103(8):1103-11, American Society for Clinical Investigation, United States (1999).

Stribling, R., et al., "Aerosol gene delivery in vivo," *Proc. Natl. Acad. Sci. USA* 89(23):11277-81, National Academy of Sciences, United States (1992).

Szabo, S.J., et al., "A novel transcription factor, T-bet, directs Th1 lineage commitment," *Cell* 100(6):655-69, Cell Press, United States (2000).

Takano, F., et al., "Protective effect of (+)-catechin against 5-fluorouracil-induced myelosuppression in mice," *Toxicology* 201:33-142, Elsevier Ireland Ltd., The Netherlands (2004).

Tomkinson, A., et al., "A murine IL-4 receptor antagonist that inhibits IL-4- and IL-13-induced responses prevents antigen-airway eosinphilia and airway hyperresponsiveness," *J. Immunol.* 166(9):5792-800, American Association of Immunologists, United States (2001).

Umetsu, D.T. and DeKruyff, R.H., "Th1 and Th2 CD4+ cells in human allergic diseases," *J. Allergy Clin. Immunol.* 100(1):1-6., Mosby, United States (1997).

Vercelli, D., "Immunoglobulin E and its regulators," *Curr. Opin. Allergy Clin. Immunol.* 1(1):61-5, Lippincott Williams & Wilkins, United States (2001).

Vercelli, D., "The regulation of IgE synthesis," *Clin. Allergy Immunol.* 16:179-96, Informa Healthcare, United States (2001).

Vestergaard, C., et al., "Overproduction of Th2-specific chemokines in NC/Nga mice exhibiting atopic dermatitis-like lesions," *J. Clin. Invest.*104:1097-105, American Society for Clinical Investigation, United States (1999).

Wang, H., et al., "Isolation of an antifungal thaumatin-like protein from kiwi fruits," *Phytochemistry* 61:1-6, Pergamon Press, England (Sep. 2002).

Webby, R.F., "Flavonol triglycoside from *Actinidia arguta* var. *giraldii*," *Phytochemistry* 30:2443-4, Pergamon Press, England (1991).

Whang, J.I., et al., "Phytochemical constituents of *Actinidia arguta*," *Kor. J Pharmacogn.* 31:357-63, Korean Society of Pharmacognosy, Korea (2000) (Abstract only).

Wills-Karp, M., et al., "Interleukin-13: central mediator of allergic asthma," *Science* 282:2258-61, American Assn. for the Advancement of Science, United States (1998).

Wüthrich, B., "Epidemiology of the allergic diseases: are they really on the increase?," *Int. Arch. Allergy Appl. Immunol.* 90:3-10, S. Karger AG, Switzerland (1989).

Yoshizawa, Y., et al., "Antiproliferative effects of small fruit juices on several cancer cell lines," *Anticancer Research* 20:4285-90, J.G. Delinassios, Greece (2000).

(56) References Cited

OTHER PUBLICATIONS

Yurt, R. and Austen, K.F., "Preparative purification of the rat mast cell chymase," *J. Exp. Med. 1*:146:1405-19, Rockefeller University Press, United States (1977).

Seoul National University Natural Products Science, Tradi-Medi Data Base, Dongbang Media Co. Ltd. (1999).

Unverified English Translation for Seoul National University Natural Products Science, Tradi-Medi Data Base, Dongbang Media Co. Ltd. (1999).

English language abstract of Japanese Patent Publication No. JP 2002-145754 A, espacenet database (2002).

Requirement for Restriction mailed Sep. 30, 2009 in U.S. Appl. No. 11/522,511, inventors Kim, S., et al., filed Sep. 18, 2006.

Non-Final Office Action mailed Mar. 5, 2010 in U.S. Appl. No. 11/522,511, inventors Kim, S., et al., filed Sep. 18, 2006.

Final Office Action mailed Feb. 1, 2011 in U.S. Appl. No. 11/522,511, inventors Kim, S., et al., filed Sep. 18, 2006.

Non-Final Office Action mailed Dec. 22, 2011 in U.S. Appl. No. 11/522,511, inventors Kim, S., et al., filed Sep. 18, 2006.

Requirement for Restriction mailed Jan. 5, 2011 in U.S. Appl. No. 12/180,723, inventors Kim, S., et al., filed Jul. 28, 2008.

Non-Final Office Action mailed Apr. 19, 2011 in U.S. Appl. No. 12/180,723, inventors Kim, S., et al., filed Jul. 28, 2008.

English language Abstract of Chinese Patent Application No. CN 1107308 A, European Patent Office, espacenet database, (1995).

English language Abstract of Korean Patent Publication No. KR 2001-0096881, European Patent Office, espacenet database, (2001).

English language Abstract of Japanese Patent Publication No. 2001-220344, European Patent Office, espacenet database, (2001).

English language Abstract of Japanese Patent Publication No. 2002-275079, European Patent Office, espacenet database, (2002).

English language Abstract of Japanese Patent Publication No. 2003-61615, European Patent Office, espacenet database, (2003).

English language Abstract of Japanese Patent Publication No. JP 2003-171294 A, Japanese Patent Office, espacenet database (2003).

English language Abstract of Japanese Patent Publication No. JP 07-061915 A, Japanese Patent Office, Patent & Utility Model Gazette database.

English language Abstract of Japanese Patent Publication No. JP 02-202808 A, Japanese Patent Office, Patent & Utility Model Gazette database.

English language Abstract of Japanese Patent Publication No. JP 62-146581 A, Japanese Patent Office, Patent & Utility Model Gazette database.

English language abstract of Russian Patent RU 2 112 524 C1, espacenet database (1998).

English language translation (machine-translated document) for Korean publication No. KR 1994-0001893 A, Korean Intellectual Property Office, http://www.kipris.or.kr.

English language translation (machine-translated document) for Korean publication No. KR 1996-004025 A, Korean Intellectual Property Office, http://www.kipris.or.kr.

Kim, Y., "Herbal extract inhibiting the interleukin-5 action," Project No. KOSEF 961-0719-112-2 (1998).

Unverified English translation of relevant portions of Kim, Y., "Herbal extract inhibiting the interleukin-5 action," Project No. KOSEF 961-0719-112-2 (1998).

Motohashi, N., et al., "Biological Activity of Kiwifruit Peel Exiracts," *Phytotherapy Research 15*:337-343, John Wiley & Sons, Ltd., England (2001).

English language Abstract of Korean Patent Publication No. KR 2001-0018160 A, European Patent Office, espacenet database (2001).

English language Abstract of Japanese Patent Publication No. JP 2001-206836 A, European Patent Office, espacenet database (2001).

English language Abstract of Japanese Patent Application No. JP 2-202808 A, European Patent Office, espacenet DB, (1990).

English language Abstract of Japanese Patent Application No. JP 7-61915 A, European Patent Office, espacenet DB, (1995).

English language Abstract of Japanese Patent Application No. JP 62-146581 A, European Patent Office, espacenet DB, (1987).

English language Abstract of Japanese Patent Application No. JP 2001-220344 A, European Patent Office, espacenet DB, (2001).

English language Abstract of Japanese Patent Application No. JP 2002-145754 A, European Patent Office, espacenet DB, (2002).

English language Abstract of Japanese Patent Application No. JP 2002-275079 A, European Patent Office, espacenet DB, (2002).

English language Abstract of Japanese Patent Application No. JP 2003-61615 A, European Patent Office, espacenet DB, (2003).

English language Abstract of Russian Patent Application No. RU 2 112 524 C1, European Patent Office, espacenet DB, (1998).

Office Action mailed Mar. 5, 2010, in U.S. Appl. No. 11/522,511, Kim, filed Sep. 18, 2006.

\* cited by examiner

COMPOSITION COMPRISING THE EXTRACT OF *ACTINIDIA ARGUTA* AND RELATED SPECIES FOR THE PREVENTION AND TREATMENT OF ALLERGIC DISEASE AND NON-ALLERGIC INFLAMMATORY DISEASE

CROSS REFERENCE TO RELATED APPLICATION

This application claims the benefit of U.S. Provisional Application No. 60/405,295 filed on Aug. 23, 2002.

FIELD OF THE INVENTION

The present invention relates to an extract of *Actinidia arguta* and related species and a composition comprising the same having preventing and treating activity of allergic disease and non-allergic inflammatory disease.

BACKGROUND OF THE INVENTION

Allergic diseases such as anaphylaxis, allergic rhinitis, asthma, atopic dermatitis, food allergies and urticaria, inflict up to 20% of the population in many countries and are increasing in prevalence (Wuthrich B., *Int. Arch. Allergy Appl. Immunol.*, 90, pp 3-10, 1989).

Allergic diseases are mediated by immunoglobulin E (IgE), while the type-2 T helper (Th2) cell, mast cell and eosinophil are proven to play important roles in that process (Maggi E., *Immunotechnology*, 3, pp 233-244, 1998; Pawankar R., *Curr. Opin. Allergy Clin. Immunol.*, 1, pp 3-6, 2001; Vercelli D., *Clin. Allergy Immunol.*, 16, pp 179-196, 2002).

Without helminth infection or other stimuli, IgE is normally one of abundant immunoglobulin isotypes found in human serum as well as several species of experimental animals (Maggi E., *Immunotechnology*, 3, pp 233-244, 1998; Coffman R L and Carty J., *J. Immunotechnology*, 136, pp 949-954, 1986). According to the "Th2 hypothesis", IgE production is favored in the immunological condition in which humoral immunity mediated by Th2 cells and related cytokines such as IL-4, IL-5 and IL-13, is predominant (Maggi E., *Immunotechnology*, 3, pp 233-244, 1998). The current view of the progress of allergic diseases is that genetic and environmental factors interact with each other, leading to the production of IL-4 through the Stat6-mediated signaling pathway and the activation of specific transcription factors such as c-Maf, GATA3, NIP45 and NFATc in native T cells, and eventually resulting in the development of allergen-specific T helper 2 CD4+ cells. Once generated, allergen-activated Th2 cells secrete IL-4, IL-5 and IL-13. IL-4 and IL-5 induce the production of IgE and IgG1 by B cells as well as the stimulation of the development of eosinophils in bone marrow and their recruitment into inflamed tissues (Erb K. J.; *Immunol. Today*, 20, pp 317-322, 1999; Rothenberg M E., *N. Engl. J. Med.*, 338, pp 1592-1600, 1998). IL-13 is a cytokine closely related to IL-4 and binds to the IL-4 receptor alpha chain inducing allergic phenotypes independently of IL-4, IgE or eosinophils (Wills-Karp M., et al., *Science*, 282, pp 2258-2261, 1998; Grunig G., et al., *Science*, 282, pp 2261-2263, 1998).

Circulating IgE binds to two isoforms of IgE receptors: high-affinity IgE receptors (FcεRI) present on the surface of mast cells and basophils, and low affinity IgE receptors (FcεRII or CD23) present on the surfaces of lymphocytes, eosinophils, platelets and macrophages. It is believed that the most important factor governing the pathogenesis of allergic disorders is the cross-linkage of IgE receptors on mast cells, after encountering allergen and the consequent degranulation of mast cells. The molecules released by mast cells include histamine, heparin, proteases and free radicals, which mediate a variety of biological effects including vasodilation, intestinal and/or bronchial smooth muscle contraction, mucous secretion and local proteolysis. Following initial immediate reaction of the mast cells, an influx of eosinophils, basophils and lymphocytes occurs 6-24 hours later. This late-phase response can lead to chronic tissue inflammation continuously exposed to antigens.

Conventional drugs for the treatment of allergic disorders include anti-histamines, steroidal or non-steroidal anti-inflammatory drugs and leukotriene antagonists. These drugs are useful mainly for symptomatic effects, and fail to provide with such treatments that the fundamental cure of allergic diseases such as alleviating excessive humoral immunity or suppressing IgE production is required. The hypothesis that reducing serum IgE level could improve allergic symptoms was demonstrated by clinical trials of the chimeric anti-IgE antibody (CGP-51901) and recombinant humanized monoclonal antibody (rhuMAB-E25) (Fahy J V et al., *Am. J. Respir. Crit. Care. Med.*, 155, pp 1828-1834, 1997). Diacyl benzimidazole analogs and bacterial polysaccharides that inhibit IgE synthesis and secretion have been described in U.S. Pat. No. 6,369,091 and U.S. patent application Ser. No. 20020041885, respectively.

The only method for fundamental treatment of allergy is carrying out immunotherapy or desensitization therapy. The immunotherapy is treatment method, which reduces hypersensitivity to allergic origin and improves allergic symptom by administering refined allergen for long period to allergic patient with gradually increasing their dosage. After their introduction in 1911, the immunotherapy has been used for treatment of allergic disease such as allergic rhinitis, allergic asthma, bee poisoning and so on by using antigen-specific IgE antibody. Major mechanism reducing hypersensitivity has not been clearly found yet, but it is known that increase of IgG concentration while reducing IgE concentration induces normal immunity reaction.

*Actinidia arguta*, *A. polygama*, and *A. kolomikta* belonged to Actinidiaceae, are distributed in Siberia, the northern area of China, North and South Korea. More than 30 species belonged to Actinidiaceae has been reported. Among those, the fruit of *A. chinensis* or *A. delicious* have been named as kiwi and *Actinidia arguta* and other same genus fruit have been used as materials of Chinese medicine named as 'mihudo' to treat liver disease, gastrointestinal disease and urogenital lithiasis without toxicity (Seoul National University Natural Products Science, *Tradi-Medi Data Base*, dongbang media Co. Ltd. 1999). However, there have been no report or suggestion about the treatment and prevention of allergic disease and non-allergic inflammatory disease using by *Actinidia* fruit.

Meanwhile, there has been concentrated effort to investigate effective anti-allergy and anti-inflammatory natural products.

Korea Patent Application No. 92-11752 disclosed an anti-inflammatory, anti-allergic and anti-rheumatic drug comprising biflavonoid such as 4'-O-methyl ochnaflavone isolated from *Lonicera japonica*, which shows various allergy or inflammation treating activity. Korea Patent Registration No. 100744 disclosed anti-inflammatory, anti-allergic and anti-rheumatic drug comprising several biflavonoid compounds isolated from the leaves of *Ginko biloba*. Several Oriental medicine recipes comprising *Siegesbeckia glabrescens* have been reported to have IgE-reducing activity (Kim H. M et al.,

*Phytother. Res.*, 15, pp 572-576, 2001). Furthermore, lots of medicinal herbs have been found to be rich sources of histamine release inhibitors or anti-inflammatory drugs.

However, there has been not reported or disclosed about anti-allergic and anti-inflammatory action of hardy kiwifruit extract in any of above literatures.

To investigate an anti-allergic and anti-inflammatory drugs among Chinese herbs, the inventors of the present invention have intensively carried out in vivo and in vitro experiments concerning the effects of hardy kiwifruit extract on the change of Th1/Th2 cytokines and IgE, IgG subtype in human serum as well as inhibition test of histamine release from mice peritoneal mast cells and rat paw edema test.

SUMMARY OF THE INVENTION

The present invention provides a pharmaceutical composition comprising the extract of hardy kiwifruit as an active ingredient in an effective amount to treat and prevent allergic disease and non-allergic inflammatory disease by reducing inflammation action, by inhibiting histamine release from mast cell, and by increasing the level of Th1 cytokines, IgG2a in serum and reducing the level of Th2 cytokines and IgE in serum.

The present invention also provides a use of above extract for the preparation of pharmaceutical composition to treat and prevent allergic disease and non-allergic inflammatory disease in mammal or human.

The present invention also provides a health food or food additives comprising above extract for prevention or alleviation of allergic disease and non-allergic inflammatory disease by reducing inflammation action, by inhibiting histamine release from mast cell, and by increasing the level of Th1 cytokines, IgG2a in serum, and reducing the level of Th2 cytokines and IgE in serum.

The present invention also provides a feed or feed additives comprising above extract for treatment and prevention of allergic disease and non-allergic inflammatory disease by reducing inflammation action, by inhibiting histamine release from mast cell, and by increasing the level of Th1 cytokines, IgG2a in serum, and reducing the level of Th2 cytokines and IgE in serum.

The present invention also provides a cosmetic composition comprising above extract as an active ingredient in an effective amount to treat, prevent and improve allergic skin disease and non-allergic inflammatory skin inflammation disease by reducing inflammation action, by inhibiting histamine release from mast cell, and by increasing the level of Th1 cytokines, IgG2a in serum, and reducing the level of Th2 cytokines and IgE in serum.

BRIEF DESCRIPTION OF THE DRAWINGS

The above and other objects, features and other advantages of the present invention will more clearly understood from the following detailed description taken in conjunction with the accompanying drawings, in which.

DETAILED DESCRIPTION OF THE INVENTION

Figure 1A:
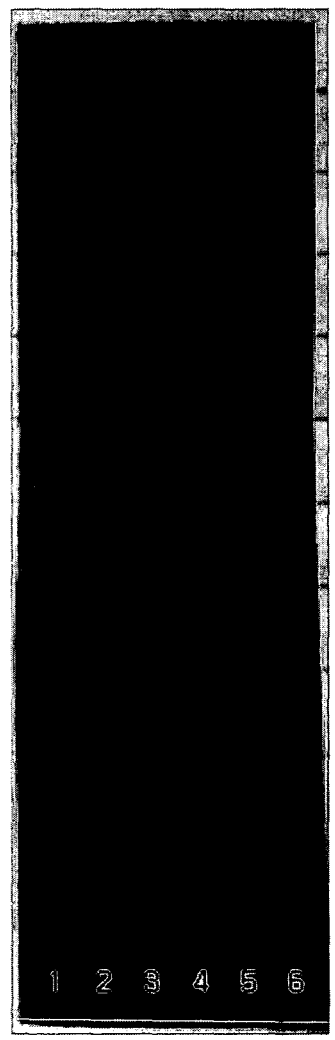
FIG. 1a shows TLC photograph of the extracts and fractions of hardy kiwifruit.

Accordingly, it is an object of the present invention to provide a pharmaceutical composition comprising the crude extract or non-polar solvent soluble extract of the hardy kiwifruit as an active ingredients for treatment and prevention of allergic disease and non-allergic inflammatory disease.

It is an object of the present invention to provide a use of a crude extract or non-polar solvent soluble extract of the hardy kiwifruit for the preparation of therapeutic agent for treatment and prevention of allergic disease and non-allergic inflammatory disease in human or mammal.

It is an object of the present invention to provide a method of treating or preventing allergic disease and non-allergic inflammatory disease in a mammal comprising administering to said mammal an effective amount of crude extract or non-polar solvent soluble extract of the hardy kiwifruit, together with a pharmaceutically acceptable carrier thereof.

It is another object of the present invention to provide a health food or food additives comprising above extract, together with a sitologically acceptable additive for prevention and improvement of allergic disease and non-allergic inflammatory disease.

It is still another object of the present invention to provide an animal feed or feed additives comprising above extract as essential components for treatment, prevention, and improvement of allergic disease and non-allergic skin inflammatory disease.

It is still another object of the present invention to provide a cosmetic composition comprising above extract for prevention and improvement of allergic disease and non-allergic inflammatory disease.

Above described allergic disease or allergic skin disease comprise anaphylaxis, allergic rhinitis, asthma, allergic conjunctivitis, allergic dermatitis, atopic dermatitis, contagious dermatitis, urticaria, insect allergies, food allergies and drug allergies.

Above described non-allergic skin inflammation disease comprise various skin trouble caused by inflammation such as pimple, acne and the like.

Above described cosmetic composition comprising the hardy kiwifruit extract having preventing and improving activity of skin inflammation.

Above described pharmaceutical composition for treatment and prevention of allergic disease can be used for the purpose of increasing the efficiency of allergy immunotheraphy.

Accordingly, the present invention also provides a pharmaceutical composition comprising the crude extract or non-polar solvent soluble extract of the hardy kiwifruit as active ingredients for allergic immunotheraphy helper.

Also, the present invention also provides a pharmaceutical composition comprising an effective amount of the crude extract or non-polar solvent soluble extract of hardy kiwifruit for treatment and prevention of non-allergic inflammatory disease.

Above described non-allergic inflammatory disease comprise various dermatitis, Systemic Lupus Erythematosus (SLE), retinal inflammation, gastritis, retinopathy, hepatitis, enteritis, pancreatitis, nephritis and so on.

Above hardy kiwifruit may comprises *Actinidia arguta, A. kolomikta, A. polygama* or and the same genus plant and may use the fruit, stem and root thereof.

Above crude extract of hardy kiwifruit can be obtained by using water, lower alcohols such as methanol, ethanol and the like, or the mixtures thereof, preferably distilled water or 70% ethanol soluble extract and above non-polar solvent soluble extract therefrom can be obtained by using non polar solvent such as hexane, ethyl acetate or dichloromethane solvent.

The pharmaceutical composition of the present invention can contain about 0.01-50% by weight of the above extract based on the total weight of the composition.

The health food of the present invention comprises above extracts as 0.01 to 80%, preferably 1 to 50% by weight based on the total weight of the composition.

Above health food can be contained in health food, health beverage etc, and may be used as powder, granule, tablet, chewing tablet, capsule, beverage etc.

An inventive extract from the hardy kiwifruit may be prepared in accordance with the following preferred embodiment.

Hereinafter, the present invention is described in detail.

An inventive extract of hardy kiwifruit can be prepared in detail by following procedures, The inventive crude extract of hardy kiwifruit can be prepared by follows; hardy kiwifruit is dried and crushed; crushed hardy kiwifruit is mixed with 5 to 25-fold, preferably, approximately 10 fold volume of distilled water, lower alcohols such as methanol, ethanol, butanol and the like, or the mixtures thereof, preferably water or 70% ethanol; the solution is treated with hot water at the temperature ranging from 20 to 100° C., preferably from 60 to 100° C., for the period ranging from 1 to 24 hours with extraction method by the extraction with hot water, cold water, reflux extraction, or ultra-sonication, with 1 to 5 times, preferably 2 to 3 times, consecutively; the residue is filtered to obtain the supernatant to be concentrated with rotary evaporator, at the temperature ranging from 20 to 100° C., preferably from 50 to 70° C. and then dried by vacuum freeze-drying, hot air-drying or spray drying to obtain dried crude extract powder of the hardy kiwifruit which can be soluble in water, lower alcohols, or the mixtures thereof.

The above crude extract of the hardy kiwifruit is stored in −20° C. to use as a sample by dissolving in distilled water to adjust to certain concentration.

Additionally, non-polar solvent soluble extract of present invention can be prepared by following procedure; the crude extract prepared by above step, is suspended with water, and then is mixed with 1 to 100-fold, preferably, 1 to 5-fold volume of non polar solvent such as ethyl acetate, chloroform, hexane and the like; the non-polar solvent soluble layer is collected to obtain non-polar solvent soluble extract of the present invention.

Also, above described procedures may be modified or subjected further step to fractionate or isolate to obtain more effective fractions or compounds by the procedure well-known in the art, for example, the procedure disclosed in the literature (Harborne J. B., *A guide to modern techniques of plant analysis*, 3$^{rd}$ Ed. pp 6-7, 1998).

To investigate the anti-allergic and anti-inflammatory activity of the hardy kiwifruit extract prepared by above procedure, in vivo and in vitro experiments such as ELISA method to determine the level of Th1/Th2 cytokines and IgE, IgG subtype in serum, inhibition test of histamine release from mast cells and anti-inflammation assay to test the effects of inventive extract was carried out and then it is confirmed that inventive extract shows excellent anti-allergic and anti-inflammatory effect.

Specifically, the reduction of allergen specific-IgE and the increase of allergen specific-IgG2a has been main purpose in immunotherapy field, the only one present fundamental treatment of allergic disease and through above experiments, therefore, it is confirmed that hardy kiwifruit can increase treating efficiency if it is used with immunotherapy as an allergic immunotheraphy aid.

In accordance with another aspect of the present invention, there is provided a pharmaceutical composition comprising the hardy kiwifruit extract prepared by above preparation method for the treatment and prevention of allergic disease and non-allergic inflammation disease as active ingredients.

It is another of the present invention to provide a treating and preventing method comprising administering a pharmaceutical composition comprising said extract prepared by above preparation method to allergic disease and non-allergic inflammatory disease of mammals including human.

The composition for treating and preventing allergic disease and non-allergic inflammatory disease may comprises above extracts as 0.01~50% by weight based on the total weight of the composition.

The inventive composition may additionally comprise conventional carrier, adjuvant or diluents in accordance with conventional using method well known in the art.

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to administer at the amount ranging 10 g/kg, preferably, 1 to 3 g/kg by weight/day of the inventive extract of the present invention. The dose may be administered in single or divided into several times per day. In terms of composition, the amount of inventive extract should be present between 0.01 to 95% by weight, preferably 0.5 to 80% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

Also, the present invention provide a composition of the health food beverage for prevention and improvement of allergic disease and non-allergic inflammation disease adding the hardy kiwifruit 0.01 to 20% by weight, amino acids 0.001 to 5% by weight, vitamins 0.001 to 2% by weight, sugars 0.001 to 20% by weight, organic acids 0.001 to 10% by weight, sweetener and flavors of proper amount.

Above the extract of hardy kiwifruit can be added to food and beverage for the prevention and improvement of allergic disease and non-allergic inflammatory disease.

To develop for health food, examples of addable food comprising above extracts of the present invention are e.g., various food, beverage, gum, vitamin complex, health improving food and the like, and can be used as power, granule, tablet, chewing tablet, capsule or beverage etc.

Also, the extract of present invention will be able to prevent, and improve allergic disease and non-allergic inflammation disease by comprising to child and infant food, such as modified milk powder, modified milk powder for growth period, modified food for growth period.

Above described composition therein can be added to food, additive or beverage, wherein, the amount of above described extract in food or beverage may generally range from about 0.1 to 95 w/w %, preferably 1 to 80 w/w % of total weight of food for the health food composition and 1 to 30 g, preferably 3 to 10 g on the ratio of 100 ml of the health beverage composition.

Providing that the health beverage composition of present invention contains above described extract as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

The inventive composition may additionally comprise one or more than one of organic acid, such as citric acid, fumaric acid, adipic acid, lactic acid, malic acid; phosphate, such as phosphate, sodium phosphate, potassium phosphate, acid pyrophosphate, polyphosphate; natural anti-oxidants, such as polyphenol, catechin, α-tocopherol, rosemary extract, vitamin C, green tea extract, licorice root extract, chitosan, tannic acid, phytic acid etc.

The above extract of the hardy kiwifruit may be 20 to 90% high concentrated liquid, power, or granule.

Similarly, the above extract of the hardy kiwifruit can comprise additionally one or more than one of lactose, casein, dextrose, glucose, sucrose and sorbitol.

Also, in the present invention, there is also provided a using method of the food additives such as sterilizer, spice, seasoning, various nutrients, vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al, or as essential component of food materials.

Wherein the food additives can be added to food by deposition, spray, or mixing the ratio of the additives is not so important but it generally range from about 0.01 to 20 w/w % per 100 w/w % present composition. Examples of addable food comprising aforementioned extract therein are.

Wherein the food additives can be added to one or one over food such as fruits, vegetables, food dehydrated foods or cutting products such as fruits, vegetables; fruit juice, vegetable juices or the mixture juices thereof; drinks containing acid-beverage; confectionaries such as cookie, candy, caramel, gum; breads; ice creams, teas, fermented milk such as yogurt; dairy product, spices, alcoholic beverages, cans, in-bottles, noodles, processed livestock products, processed marine products, fermented food, beans food, cereals food, processed meats, licorices or hubs.

In accordance with another aspect of the present invention, there are provided a feed or feed additive essentially comprising said extract prepared by above preparation method for prevention and improvement allergic disease and non-allergic disease.

Above food additives is characterize of mixing amount of 5 to 100 g per 1 kg by weight based on the total dried weight of the feed.

Furthermore, the present invention provides a feed composition comprising above feed additives.

Also, the present invention also provides a cosmetic composition comprising an effective amount of the crude extract or non-polar solvent soluble extract of hardy kiwifruit for prevention and improvement of allergic disease or non-allergic inflammatory disease.

The present cosmetic composition provide cosmetic composition comprising the above extracts with 0.01 to 30%, more preferably, 0.01 to 5% by the weight of the inventive composition based on the total weight of the composition for the treatment, prevention, and improvement allergic skin disease and non-allergic skin inflammation disease.

The other components may be a mixture of the ingredients of a conventional cosmetic composition well known in the art.

Cosmetic formulations containing above composition may be prepared in any form such as skin, lotion, cream, essence, toner, emulsion, pack, soup, shampoo, rinse, cleanser, body washing solution, washing solution, treatment, gel, balm, spray solution and the like.

The cosmetic composition of the present invention can comprises additional additives selected from the group consisting of water soluble vitamin, lipid soluble vitamin, peptide polymer, polysaccharide polymer, sphingolipid and seaweed extract.

Preferable water soluble vitamins are any one which can be mixed with cosmetic, however, various vitamin such as vitamin B1, B2, B6, pyridoxine, pyridoxine HCl, vitamin B12, pantothenic acid, nicotinic acid, nicotinamide, folic acid, vitamin C, vitamin H etc, their salt thereof such as thiamin HCl salt, ascorbic acid Na salt etc or their derivatives thereof such as ascorbic acid-2-phosphonic acid Na salt, ascorbic acid-2-phosphonic acid Mg salt are preferable and those can be obtained by conventional method such as microbial conversion method, purification method from the microbial cultivates, enzymatic method or chemical synthetic method.

Preferable lipid soluble vitamins are any one which can be mixed with cosmetic, however, various vitamin such as vitamin A, D2, D3, E (dl-α-tocopherol, d-α-tocopherol, d-δ-tocopherol) and their derivatives such as palmitic acid ascorbate, stearic acid ascorbate, dipalmitic acid ascorbate, acetic acid-dl-α-tocopherol, nicotinic acid dl-α-tocopherol vitamin E, dl-pantothenyl alcohol, D-pantothenyl alcohol, pantothenyl ethylether etc. containing the lipid soluble vitamin used in examples of present invention are preferable and those can be obtained by conventional method such as microbial conversion method, purification method from the microbial cultivates, enzymatic method or chemical synthetic method.

Preferable peptide polymers are any one which can be mixed with cosmetic, however, collagen, hydrolysable collagen, gelatin, elastin, hydrolysable gelatin, keratin etc. containing the peptide polymer used in examples of present invention are preferable.

Preferable polysaccharide polymers are any one which can be mixed with cosmetic, however, hydroxy ethyl cellulose, xanthin gum, hyaluronic acid Na, chondroitin sulfate or their salt (Na salt etc) and the like are preferable. For example, chondroitin sulfate or the salt thereof etc can be used by being purified from mammal or fishes ordinarily.

Preferable sphingolipid are any one, which can be mixed with cosmetic, however, ceramide, pit-sphingosin, sphingo-lipopolysaccharide and the like are preferable. Sphingo-lipid can be obtained by being purified from mammal, fish, shellfish, yeast or plant etc in conventional method.

Preferable seaweed extract is any one which can be mixed with cosmetic, however, the extract of brown algae, red algae, green algae and the like or the purified carrageenan, alginic acid, arginic acid Na, K isolated therefrom are preferable. Algae extract can be obtained by being purified from seaweed in conventional method.

The cosmetic composition of the present invention may combine with other ingredients combined with conventional cosmetic composition, if necessary, together with above described essential ingredient.

Preferable above described other ingredients may comprises oil ingredient, humectants, emollients, surface active agents, organic or inorganic dye, organic powder, ultraviolet ray absorbing agent, preservatives, antiseptics, antioxidants, plant extract, pH controller, alcohol, pigments, perfumes, refrigerants, blood circulator, antihidrotic, distilled water etc.

Preferable oil ingredients may comprise ester oil, hydrocarbon oil, silicone oil, fluoride oil, animal oil, plant oil and so on.

Preferable ester oil described above may comprise glyceryl tri-2-ethyl hexanoic acid, cetyl 2-ethyl hexanoic acid, isopropyl myristic acid, butyl myristic acid, isopropyl palmitic acid, ethyl stearic acid, octyl palmitic acid, isocetyl isostearic acid, butyl stearic acid, ethyl linoleic acid, isopropyl linoleic acid, ethyl oleic acid, isocetyl myristic acid, isostearyl myristic acid, isostearyl palmitic acid, octyldodecyl myristic acid, isocetyl isostearic acid, diethyl sebasic acid, isopropyl adipic acid, isoalkyl neopetanoic acid, glyceryl tri(capryl, capric acid), trimethylopropane tri-2-ethyl hexanoic acid, trimethylopropane triisostearic acid, pentaerythritol tetra-2 ethyl hexanoic acid, cetyl caprylic acid, decyl lauric acid, hexyl lauric acid, decyl myristic acid, myristyl myristic acid, cetyl myristic acid, stearyl stearic acid, decyl oleic acid, cetyl licinoleic acid, isostearyl lauric acid, isotridecyl myristic acid, isocetyl palmitic acid, octyl stearic acid, isocetyl stearic acid, isodecyl oleic acid, octyldodecyl oleic acid, octyldodecyl linoleic acid, isopropyl isostearic acid, cetostearyl 2-ethyl hexanoic acid, stearyl 2-ethyl hexanoic acid, hexyl isostearic acid, ethylene glycol dioctanoic acid, ethylene glycol dioleic acid, propylene glycol dicapric acid, propylene glycol di(capryl, capric acid), propylene glycol dicaprylic acid, neopentylglycol dicapric acid, neopentylglycol dioctanoic acid, glyceryl tricaprylic acid, glyceryl triundecylic acid, glyceryl triisopalmitic acid, glyceryl triisostearic acid, octyldodecyl neopentanoic acid, isostearyl octanoic acid, octyl isononanoic acid, hexyldecyl neodecanoic acid, octyldodecyl neodecanoic acid, isocetyl isostearic acid, isostearyl isostearic acid, octyldecyl isostearic acid, polyglycerin oleanoic acid ester, polyglycerin isostearic acid ester, triisocetyl citric acid, triisoalkyl citric acid, triisooctyl citric acid, lauryl lactic acid, myristyl lactic acid, cetyl lactic acid, octyldecyl lactic acid, triethyl citric acid, acetyltriethyl citric acid, acetyl tributyl citric acid, trioctyl citric acid, diisostearyl maleic acid, di 2-ethylhexyl hydroxy stearic acid, 2-ethyl hexyl succinic acid, diisobutyl adipic acid, diisopropyl sebasinic acid, dioctyl sebacinic acid, cholesteryl stearic acid, cholesteryl isostearic acid, cholesteryl hydroxy stearic acid, cholesteryl hydroxy stearic acid, cholesteryl oleic acid, dihydrocholesteryl oleic acid, pitsteryl isostearic acid, pitsteryl oleic acid, isocetyl 12-stealoyl hydroxy stearic acid, stearyl 12-stealoyl hydroxy stearic acid, isostearyl 12-stealoyl hydroxy stearic acid.

Preferable hydrocarbon oil described above may comprise squalene, liquid paraffin, α-olefin oligomer, isoparaffin, ceresin, paraffin, liquid isoparaffin, polybuden, microcrystalline wax, vaselin and the like.

Preferable silicone oil may comprise polymethylsilicone, methylphenylsilicone, methylcyclopolysiloxane, octamethylpolysiloxane, decamethylpolysiloxane, dodecamethylcyclosiloxane, dimethyl siloxane-methyl cetyloxysiloxane copolymer, dimethyl siloxane-methyl stealloxysiloxane copolymer, alkyl modified silicone oil, amino modified silicone oil and the like.

Preferable fluoride oil can comprise perfluoropolyether and the like.

Preferable animal or plant oil can comprise avocado oil, almond oil, olive oil, sesame oil, rice husk oil, safflower oil, soy-bean oil, corn oil, rape oil, amygdalin oil, palm kernel oil, palm oil, pimaja oil, sunflower oil, fruite seed oil, cotton seed oil, coconut palm oil cucui nut oil, wheat embryo bud oil, rice embryo bud oil, sia butter, evening-primrose oil, marker daymia nut oil, medo home oil, egg yolk oil, lanolin, hempseed oil, mink oil, orange ruppy oil, hohoba oil, carnawa wax, liquid lanolin, solid pimaja wax and the like.

Preferable humectants can comprise water-soluble low molecular humectants, lipophilic low molecular humectants, water-soluble polymer and lipid soluble polymer.

Specifically, preferable water soluble low molecular humectants can comprise cerin, glutamine, sorbitol, mannitol, pyrrolidone-carboxylic acid Na, glycerin, propylene glycol, 1,3-butylene glycol, ethylene glycol, polyethylene glycol (polymerization index. >2), polypropylene glycol (polymerization index >2), lactic acid, lactate salt and the like.

Preferable lipid soluble low molecular humectants can comprise cholesterol, cholesteryl ester and the like.

Preferable water-soluble polymer can comprise carboxy vinyl polymer, poly asparaginic acid salt, tragacanth, xanthin gum, HMC (hydroxy methyl celluose), HEC (hydroxy ethyl celluose), HPC (hydroxy propyl celluose), carboxymethylcellulose, water-soluble chitin, chitosan, dextrin and the like.

Preferable lipid soluble polymer can comprise polyvinylpyrrolidone-eicocene copolymer, polyvinylpyrrolidone-hexadecene copolymer, nitrocellulose, dextrin fatty acid ester, silicone polymer and the like.

Preferable emollients can comprise long chain acyl glutamic acid cholesteryl ester, cholesteryl hydroxy stearic acid, 12-hydroxy stearic acid, rogic acid, lanolin fatty acid cholesteryl ester and the like.

Preferable surface-active agent can comprise nonionic surfactants, anionic surfactants, cationic surfactants, amphivalent surfactants and the like.

Specifically, preferable non-ionic surfactants can comprise self-emulsified monostearic acid glycerin, propylene glycol fatty acid ester, glycerin fatty acid ester, polyglycerin fatty acid ester, sorbitan fatty acid ester, polyoxyethylene (POE) sorbitan fatty acid ester, POE sorbitan fatty acid ester, POE glycerin fatty acid ester, POE alkyl ether, POE fatty acid ester, POE solid pimaja oil, POE pimaja oil, POE-POP copolymer, POE-POP alkyl ether, polyether modified silicone, lauric acid alkanol amide, alkyl amine oxide, hydrogen addition soybean phospholipid and the like.

Preferable anionic surfactants can comprise fatty acid soap, α-acyl sulfonic acid salt, alkyl sulfonic acid salt, alkyl ally sulfonic acid, alkyl naphthalene sulfonic acid salt, alkyl sulfonic acid salt, POE alkylether sulfate salt, alkyl amide sulfate salt, alkyl phosphate salt, POE alkyl phosphate salt, alkylamide phospahate salt, alkyloylalkyl taurine salt, N-acyl-amino acid salt, POE alkyl ether carboxylic acid salt, alkyl sulfo succinic aid salt, alkyl sulfo-acetic acid salt, acylated hydrolysable collagen peptide salt, perfluoro alkyl phosphate ester and the like.

Preferable cationic surfactant can comprise alkyl trimethyl ammonium chloride, stearyl trimethyl ammonium chloride, stearyl trimethyl ammonium bromide, setostearyltrimethyl ammonium chloride, distearyl dimethyl ammonium chloride, stearyl dimethyl benzyl ammonium chloride, vehenyltrimethyl ammonium bromide, benzalkonium chloride, diethylamino ethyl amide stearic acid, dimethylaminopropyl amide stearic acid, lanolin derivatives quaternary ammonium and the like.

Preferable ambivalent surfactants can comprise carboxy betaine type, amide betaine type, hydroxy sulfo betaine type, phosphpobetaine type, aminocarboxylic acid, imidazoline derivatives type, amide amine type and the like.

Preferable organic and inorganic dyes can comprise silicic acid, anhydrous silicic acid, magnesium silicic acid, talc, ceracyte, mica, kaolin, bengala, clay, bentonite, titan film mica, oxy chlorine bismuth, zirconium oxide, magnesium oxide, zinc oxide, titan oxide, aluminium oxide, calcium sulfate, barium sulfate, magnesium sulfate, calcium carbonate, magnesium carbonate, ferrous oxide, chromium oxide, chromium hydroxide, calamine, carbon black and the combination thereof as an inorganic dyes; polyamide, polyester, polypropylene, polystyrene, polyurethane, vinyl resin, urea resin, phenol resin, fluoride resin, silicone resin, acryl resin, melamine resin, epoxy resin, polycarbonate resin, divinyl benzene-styrene copolymer, silk powder, cellulose, CI pigment yellow, CI pigment orange as an organic dyes; and their complex etc.

Preferable organic powder can comprise metal soap such as calcium stearate; alkyl phosphonate metal salt such as sodium zinc cetylic acid, zinc laurylic acid, calcium laurylic acid; acylamino acid polyvalent metal salt such as calcium N-lauroyl-β-alanine, zinc N-lauroyl-β-alanine, calcium N-lauroyl-glycine etc.; amide sulfonic acid polyvalent metal salt such as calcium N-lauroyl-taurine, calcium N-palmitoyl-taurine; N-acyl basic amino acid such as Nε-lauroyl-L-lysine, Nε-palmitoyl-lysine, Nα-palmitoyl ornitine, Nα-lauroly arginine, hardened lanolin fatty acid acyl arginine and the like; N-acylpolypeptide such as N-lauroylglycyl glycine; α-amino fatty acid such as α-amino caprylic acid, α-amino lauric acid and the like; polyethylene, polypropylene, nylon, polymethylmetacrylate, polystyrene, divinylbenzene-styrene copolymer, ethylene tetrafluoride and so on.

Preferable ultraviolet absorbing agents can comprise paraaminobenzoic acid, paraamonoethyl benzoate, paraamino amyl benzoate, paraamino octyl benzoate, ethyleneglycol salicylate, phenyl salicylate, octyl salicylate, benzyl salicylate, butylphenyl salicylate, homomentyl salicylate, benzyl cinnamic acid, paramethoxy 2-ethoxy ethyl cinnamic acid, paramethoxy octyl cinnamic acid, diparamethoxy mono-2-ethylhexane glyceryl cinnamic acid, paramethoxy isopropyl cinnamic acid, diisopropyl-diisopropyl cinnamate ester mixture, urokanic acid, ethyl urokanic acid, hydroxy methoxy benzophenone, hydroxymethoxy benzophenone sulfonic acid and the salt thereof, dihydroxy methoxy benzophenone, dihydroxy methoxy benzophenone disulfonate Na, dihydroxy benzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl)benzotriazole and the like.

Preferable preservatives can comprise hinokitiol, trichloric acid, trichlorohydroxydiphenylether, chlorohexidine glucuronate, phenoxyethanol, resorcine, isopropylmethylphenol, azulene, salicylic acid, zinc pilithione, bezalconium HCl, photosensitizer 301, mononitroguaiacol Na, undecylenic acid etc.

Preferable antioxidants can comprise butylhydroxyanisole, propyl gallate, ellisorbate and the like.

Preferable pH controller can comprise citric acid, sodium citrate, malic acid, sodium malate, fumaric acid, sodium fumaric acid, succinic acid, sodium succinic acid, sodium hydroxide, sodium hydrogen phosphate and the like.

Preferable alcohol can comprise cetyl alcohol etc.

Furthermore, other ingredient addable to above described component and the amount thereof is not limited within the scope of the purpose and effect of the present invention, however, it is preferable that the amount of the other ingredients ranges from 0.01 to 5%, more preferably, 0.01 to 3% in that of total composition.

The cosmetic composition of the present invention can be modified as a solution, emulsion, cohesive mixture etc.

Above described ingredients such as water-soluble vitamin, lipid soluble vitamin, peptide polymer, polysaccharide polymer, sphingolipid, sea weed extract and addable ingredients which can be added other than above described ingredients if necessary, can be obtained by conventional methods disclosed in the literature (Matsumoto Mithio, *Manual for the development of transdermal applied preparation*. Seisi Press, 1st Ed., 1985).

Additionally, the present invention also provides a cosmetic additives comprising above extract as an essential component for prevention or improvement of allergic disease and non-allergic disease.

Above cosmetic additives can be used by adding to existing cosmetics and washing solution to prevent, improve or treat allergic disease and non-allergic skin disease.

Furthermore, above cosmetic additives can be used to cream, lotion, message pack, and body washing solution, soup, shampoo and the like.

Inventive extract of the present invention have no toxicity and adverse effect therefor; they can be used with safe.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Examples and Experimental Examples are intended to further illustrate the present invention without limiting its scope.

Example 1

Preparation of Hardy Kiwifruit Extract 1-1. Preparation of Water Extract of Hardy Kiwifruit 100 g of dried hardy kiwifruit and dried stem of hardy kiwifruit (*Actinidia arguta*), dried fruit of *A. kolomikta* and *A. polygama* purchased from Kyung-dong Market located in Seoul was crushed, mixed with 1 L of distilled water and subjected to reflux extraction for 3 hrs at 90~95° C. with three times and the extract was filtered with filter paper, concentrated using by rotary evaporator (N-1000, Eyela Co. Japan) at 55~65° C. under reduced pressure and dried with freezing dryer to obtain 15.6 g of dried fruit extract, 10.4 g of dried stem extract of kiwifruit (*Actinidia arguta*), 16.2 g and 17.0 g of dried fruit extract of *A. kolomikta*, and *A. polygama* respectively. The dried powder was dissolved in distilled water (100 mg/ml).

1-2. Preparation of Water-Alcohol Soluble Extract of Hardy Kiwifruit

Except using various mix ratio of water-alcohol solvent mixture such as 30%, 50%, and 70% ethanol solvent with as an extracting solvent, all the procedure was identical to those of Example 1-1. As a result, 11 g~13 g of dried power of hardy kiwifruit was obtained at each ratio of solvent mixture and the dried powder was dissolved in distilled water (100 mg/ml).

Example 2

Preparation of Polar Solvent and Non-Polar Solvent Soluble Hardy Kiwifruit Extract The water extract prepared in Example 1-1 was subject to fractionation by following procedure.

2-1. Preparation of Chloroform Soluble Fraction 50 ml of distilled water was added to 5 g of hardy kiwifruit extract obtained in Example 1-1. 50 ml of chloroform was added thereto in separatory funnel, shaken vigorously to divide into chloroform soluble layer and water soluble layer.

2-2. Preparation of Ethyl Acetate Soluble Fraction

Above water soluble layer obtained in Example 1-1 was mixed with 50 ml of ethyl acetate and then divided into ethyl acetate soluble layer and water soluble layer.

Above chloroform soluble layer, ethyl acetate soluble layer and water layer were concentrated by rotary evaporator, dried with freeze dryer to obtain 0.34 g of chloroform soluble fraction, 0.05 g of ethyl acetate soluble fraction and 4.61 g of water fraction powders respectively.

Example 3

Fractionation of Hardy Kiwifruit Extract by Silica Gel Column Chromatography 2,784 mg of ethyl acetate soluble fraction in Example 2-2 was further subjected to silica gel column chromatography (Daiso gel IR-60-W-40: 63 mm). The developing solvent was started with chloroform:methanol:water ([1] 90:11:1, [2] 60:10:1, [3] 60:20:2) solvent mixture and ended with methanol[4] with eluting speed of 300 ml/hr to obtain four sub-fractions ([1] 2,381 mg, [2] 135 mg, [3] 148 mg, [4] 98 mg).

Above water extract, ethyl acetate soluble fraction and four sub-fractions were subjected to TLC (TLC plate: Merck Co. Ltd., Developing solvent; chloroform:methanol:water=9:5:1) and the results were shown in FIG. 1a. As shown in FIG. 1a, lane 1 is water extract, lane 2 is ethyl acetate soluble fraction, lane 3 is [4] sub-fraction, lane 4 is [3] sub-fraction, lane 5 is [2] sub-fraction and lane 6 is [1] sub-fraction.

Figure 1B:
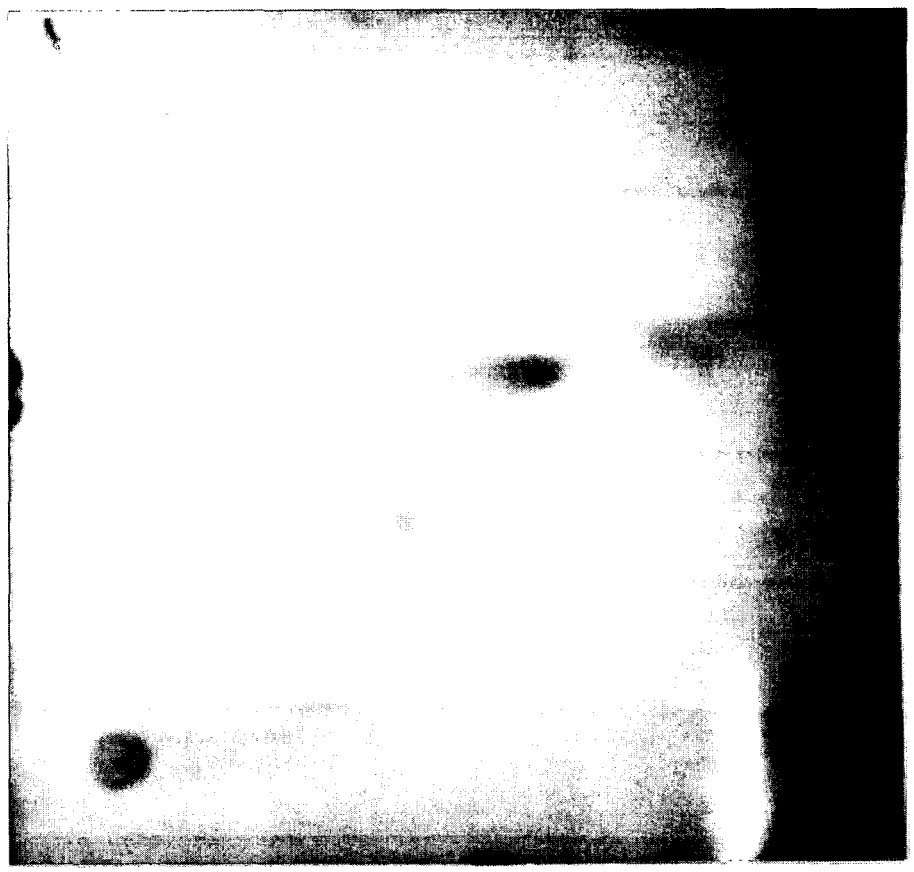
FIG. 1b shows 2D-TLC photograph of [1] sub-fraction.
Figure 1C:
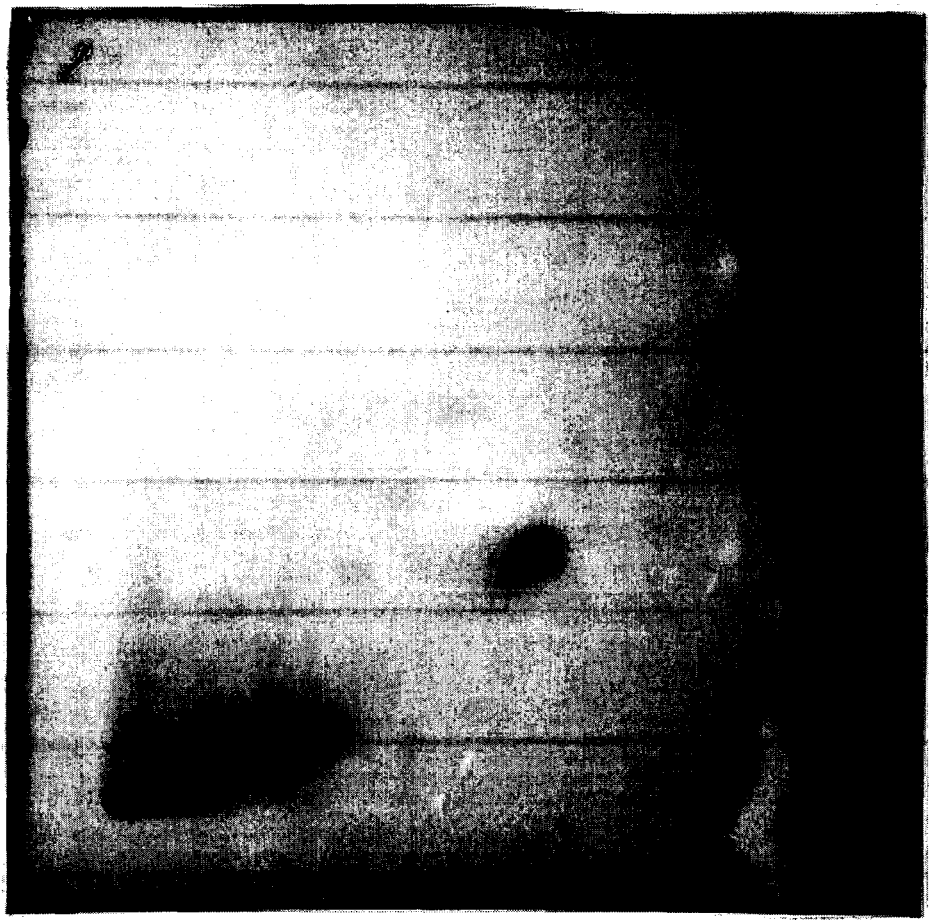
FIG. 1c shows 2D-TLC photograph of [2] sub-fraction.

Above [1] and [2] sub-fractions were subjected to 2D-TLC using chloroform:methanol:water (9:5:1) solvent mixture as a 1st developer and chloroform:acetone:water (3:8:0.5) solvent mixture as a 2nd developer (See FIG. 1b and FIG. 1c).

Experimental Example 1

Inhibition of IgE Production U266B1 Cell Line by Hardy Kiwifruit Extract 1-1. Effect of Hardy Kiwifruit Extract on IgE Production To confirm the inhibitory effect of hardy kiwifruit extraction on IgE production, U266B1 cell (lymphoblastoma cell line) was used. U266B1 is cell line of human B cell, which produces IgE.

U266B1 cells (American Type Culture Collection, Manassas, Va.) was cultured at 37° C. under 5% $CO_2$ circumstances in 24-well culture plate containing RPMI-1640 medium (15% FBS, 2 mM L-glutamine, 10 mM HEPES, 1 mM sodium pyruvate, 50 μg streptomycin and 100 U/ml penicillin). Cells were adjusted at the concentration of $2 \times 10^5$ cell/well and treated with LPS (2 μg/ml) and 100 μg/ml of hardy kiwifruit extract prepared in Example 1-1 and 1-2. Control was treated with 2 μM dexamethasone or medium (RPMI-1640). After treatment, cells were cultured for 7 days and IgE concentration of medium was measured by ELISA kit (PharMingen; San Diego, Calif.).

As shown in the Table 1, all of the water extracts of hardy kiwifruit, *A. kolomikta*, and *A. polygama* showed the inhibitory effect on IgE production as much as dexamethasone (control). Also, hardy kiwifruit 70% ethanol extract showed the strongest activity among all the three kinds of inventive hardy kiwifruit alcohol extract. The stem extract of hardy kiwifruit showed similar effect to those of above hardy kiwifruit extracts.

TABLE 1

| LPS stimulation | Treatment | IgE (IU/ml) |
|---|---|---|
| − | Medium | 187.8 ± 8.4 |
| + | Medium | 392.9 ± 3.4 |
| + | Hardy kiwifruit water extract | 228.8 ± 7.1 |
| + | *Actinidia kolomikta* water extract | 233.2 ± 5.8 |
| + | *Actinidia polygama* water extract | 211.7 ± 7.9 |
| + | Hardy kiwifruit stem extract | 241.5 ± 5.8 |
| + | Hardy kiwifruit 30% ethanol extract | 306.2 ± 16.5 |
| + | Hardy kiwifruit 50% ethanol extract | 266.8 ± 17.0 |
| + | Hardy kiwifruit 70% ethanol extract | 201.9 ± 27.6 |
| + | Dexamethasone | 203.6 ± 30.9 |

1-2. Effect of Ethyl Acetate Soluble Fraction of Hardy Kiwifruit on IgE Production To compare the inhibitory effect on IgE production of U266B1 cell, chloroform soluble fraction, ethyl acetate soluble fraction and water soluble fraction which were prepared in above Example 2 were subjected to the identical experiment disclosed in above Experimental Example 1-1.

The chloroform soluble fraction, ethyl acetate soluble fraction and water soluble fraction were treated to U266B1 cell line (at 30 μg/ml).

As shown in the Table 2, ethyl acetate soluble fraction showed stronger inhibitory effect on IgE production than that of Dexamethasone (control).

TABLE 2

| LPS stimulation | Treatment | IgE (IU/ml) |
|---|---|---|
| − | Medium | 117.4 ± 7.6 |
| + | Medium | 212.5 ± 11.8 |
| + | Hardy kiwifruit water extract | 151.7 ± 11.9 |
| + | Chloroform fraction | 206.7 ± 15.6 |
| + | Ethyl acetate fraction | 123.3 ± 8.1 |
| + | Water fraction | 218.9 ± 13.3 |
| + | Dexamethasone | 138.9 ± 2.1 |

1-3. Effect of Silica Gel Column Chromatography Fraction on IgE Production

Silica gel column chromatography fraction [1], [2], [3] and [4] prepared in Example 3 were subjected to the identical experiment disclosed in Experimental Example 1-1 to compare the inhibitory effect of IgE production on U266B1 cell.

Silica gel column chromatography fraction [1], [2], [3] and [4] were treated to U266B1 cell line (at 10 μg/ml).

As the result of Table 3, silica gel column chromatography fraction [1], [2] showed the inhibitory activity on IgE production.

TABLE 3

| LPS stimulation | Treatment | IgE (IU/ml) |
|---|---|---|
| − | Medium | 379.7 ± 13.2 |
| + | Medium | 540.4 ± 35.1 |
| + | Ethyl acetate fraction | 298.1 ± 9.7 |
| + | Silica gel fraction 1 | 293.5 ± 12.5 |
| + | Silica gel fraction 2 | 307.6 ± 24.1 |
| + | Silica gel fraction 3 | 453.1 ± 17.3 |
| + | Silica gel fraction 4 | 396.9 ± 26.8 |
| + | Dexamethasone | 277.6 ± 12.4 |

Experimental Example 2

Anti-Allergic Effect of Hardy Kiwifruit Extract in Ovalbumin-Sensitized Mouse Model 2-1. Preparation of Ovalbumin-Sensitized Mouse Model The ovalbumin-sensitized mouse model is commonly used as animal model of allergy. Female BALB/c mice, aged 6 weeks (Seoul national university animal experimental center) were adapted to the environment for 7 days. At the time of 7 weeks after birth, 100 μl of emulsion, mixed 25 μg of ovalbumin (chicken egg albumin, crude grade V, Sigma Co., Ltd.) with 2.25 mg of aluminum hydroxide (ImujectAlum, Pierce Co., Ltd.) was injected into mouse peritoneal cavity and 14 days after, it was injected once more for boosting.

And then 30 mice were divided into 3 groups and each group was orally administered with the hardy kiwifruit water extract of Example 1-1 (300 μg/mouse/day), dexamethasone (10 μg/mouse/day), or drinking water (100 μg/mouse/day) for 11 days, respectively. On the 25th day, mice were sacrificed and blood serum and spleen was collected therefrom.

2-2. Concentration Analysis of Ovalbumin-Specific IgE, IgG1, IgG2a, IgG2b in Serum In serum collected in Example 2-1, the serum levels of ovalbumin-specific IgE, IgG1, IgG2a and IgG2b were measured by ELISA kits (PharMingen Co., Ltd).

As shown in Table 4, it shows that relative concentration of each antibody of the ovalbumin-sensitized mouse to that of normal mouse. In the mouse administered with the water extract of hardy kiwifruit, ovalbumin-specific IgE level was decreased under ⅓ and IgG1 level was significantly decreased. The IgE and IgG1 level was similarly decreased in dexamethasone-administered mouse.

The IgG2a level associated with cellular immunity, was increased above 2 times in the mouse administered with the hardy kiwifruit water extract, however it was not increased in the dexamethasone-administered mouse.

It showed that the hardy kiwifruit extract could improve fundamental allergic constitution by decreasing IgE, which induces allergic symptoms, and increasing IgG2a related to normal immunity simultaneously. It is also clear that hardy kiwifruit can increase treatment efficiency when it is used with immunotherapy as an allergic immunotheraphy helper since the reduction of allergen specific-IgE and the increase of allergen specific-IgG2a have been their main purpose in immunotherapy field.

TABLE 4

|  | Normal | Drinking water | Hardy kiwifruit extract | Dexamethasone |
| --- | --- | --- | --- | --- |
| IgE | 1.0 ± 0.0 | 7.6 ± 0.2 | 2.2 ± 0.5 | 2.0 ± 0.6 |
| IgG1 | 1.0 ± 0.0 | 5.1 ± 0.1 | 3.3 ± 0.3 | 3.1 ± 0.3 |
| IgG2a | 1.0 ± 0.1 | 2.1 ± 0.4 | 4.6 ± 0.3 | 1.9 ± 0.4 |
| IgG2b | 1.0 ± 0.0 | 1.4 ± 0.1 | 1.5 ± 0.2 | 1.2 ± 0.1 | unit: pg/ml 2-3. Expression Analysis of Cytokines by Splenocytes

To analyze the expression of cytokines by the splenocytes of mouse administered with the hardy kiwifruit extract, splenocytes was prepared from spleen prepared in Example 2-1 as follows.

Each prepared splenocytes was pooled and homogenized under an aseptic condition.

Splenocytes were washed with RPMI-1640 medium, filtered through nylon mesh (60 μm pore size) to eliminate large clots, centrifuged (1500 rpm, 5 mins) to separate a precipitated cells, and then cells were added to RPMI-1640 medium supplemented with 10% FBS.

Splenocytes prepared as above were inoculated in 24-well plate ($5 \times 10^6$ cell/ml/well), treated with 100 μg/ml of ovalbumin, and incubated at 37° C. under an atmosphere containing 5% $CO_2$ for 3 days. After cultivation was finished, a culture solution was gathered and then the concentration of cytokines (IL-4, IL-5, IL-12 and interferon-γ) related to allergy were measured by commercial ELISA kits.

As shown in the Table 5, splenocytes of mouse administered with the hardy kiwifruit extract had the decreased level of IL4 and IL-5 (which comes to Th2 cytokines that is to induce allergy) and has the increased level of IL-12 and interferon-γ (which comes to Th1 cytokines that is to repress allergy). In the case of dexamethasone-treated mouse, both of Th1 and Th2 cytokines were decreased.

It is confirmed that the hardy kiwifruit extract can prevent and improve allergic disease by increasing Th1 cytokines as well as decreasing Th2 cytokines specifically, while dexamethasone suppresses the whole immune system.

Experimental Example 3

Down Regulation of Th1/Th2 Cytokines in Human PBMC

Human peripheral blood mononuclear cells (PBMCs) were prepared with Ficoll-hypaque from the whole blood of an allergy patient having a high basal serum level of IgE and cultured in RPMI media with 10% FBS. PBMCs were treated together with the hardy kiwifruit extract (at 100 μg/ml) and phytohemagglutinin (PHA, at 5 μg/ml), a commonly used lectin with an immune stimulating effect, and cultured at 5% $CO_2$ and 37° C. Forty-eight hours later, the level of IL-5, IL-13, IL-10 and Interferon-γ in cell culture supernatant was measured using ELISA.

Table 6 shows that the hardy kiwifruit extract significantly reduced the serum level of Th2 cytokines: the levels of IL-5 and IL-13 were reduced by 52% and 47%, respectively, whereas the serum level of Interferon-γ, a Th1 cytokine, was increased by 3.2 folds. This result suggested that hardy kiwifruit extract could increase the level of Th1 cytokines, while simultaneously decreasing the level of Th2 cytokines. It has been previously reported that down-regulation of Th2 cytokines could contribute to the alleviation of IgE synthesis and allergic inflammation.

TABLE 5

|  | OVA-stimulated mouse | | |
| --- | --- | --- | --- |
| | Normal mouse | Drinking water | Hardy kiwifruit extract | Dexamethasone |
| IL-4 | 21.6 ± 11.8 | 159.5 ± 15.7 | 76.5 ± 10.0 | 23.2 ± 8.7 |
| IL-5 | 0.5 ± 0.8 | 2573.6 ± 42.0 | 1638.3 ± 33.3 | 884.1 ± 80.7 |
| IL-12 | 1626.0 ± 58.5 | 906.2 ± 66.0 | 1321.2 ± 92.4 | 297.7 ± 16.4 |
| Interferon-γ | 14.1 ± 19.6 | 1016.0 ± 25.6 | 1688.2 ± 15.8 | 470.5 ± 38.6 | unit: pg/ml

TABLE 6

| PHA stimulation | Treatment | IL-5 | IL-13 | IL-10 | Interferon-γ |
|---|---|---|---|---|---|
| − | — | 92.2 ± 6.4 | 0 ± 0 | 0 ± 0 | 53.3 ± 30.2 |
| + | Medium | 518.1 ± 120.3 | 667.8 ± 46.5 | 480.3 ± 15.3 | 334.1 ± 277.7 |
| + | Hardy kiwifruit extract | 248.5 ± 62.0 | 355.7 ± 93.1 | 570.2 ± 56.3 | 1067 ± 345.1 | unit: pg/ml

Experimental Example 4

Reduction of the Human Serum Level of IgE

To test whether hardy kiwifruit extract reduces the serum level of IgE in humans or not, two allergy patients (Patients K and E with allergic rhinitis and allergic dermatitis, respectively, showing high basal serum levels of IgE) were orally administered with hardy kiwifruit extract (1 g in dry weight) on a daily basis over a 21-day period, and their serum levels of IgE were measured every two weeks by ELISA method.

At the result of experiment, it was shown that the serum levels of IgE in the two patients were reduced continuously by ⅔ after 42 days and the dermatitis symptom of patient E were also improved during the period of experiment (See Table 7).

TABLE 7

|  | 1 day | 14 day | 28 day | 42 day |
|---|---|---|---|---|
| Patient K | 950.8 IU/ml | 855.6 IU/ml | 679.1 IU/ml | 266.1 IU/ml |
| Patient E | 278.3 IU/ml | 236.0 IU/ml | 189.2 IU/ml | 95.0 IU/ml |

Experimental Example 5

Inhibition of Histamine Release from Mice Peritoneal Mast Cells

The release of histamine from mast cells is one of the major causes of allergic reactions. Therefore, the effects of hardy kiwifruit extract were tested on histamine release from mast cells.

Each mouse was anesthetized with ether, and injected with 20 ml of Tyrode buffer B (NaCl, glucose, $NaHCO_3$, KCl, $NaH_2PO_4$) containing 0.1% gelatin into the peritoneal cavity; then the abdomen was gently massaged for about 90 seconds. The peritoneal cavity was carefully opened, and the fluid containing peritoneal cells was aspirated by pasteur pipette. The peritoneal cells were then sedimented at 150×g for 10 min. at room temperature and resuspended in Tyrode buffer B. Mast cells were separated from the major components of rat peritoneal cells as described in the literature (Yurt et al., *J Exp Med.*, 1; 146(5), pp 1405-19, 1977). Peritoneal cells suspended in 1 ml of Tyrode buffer B were layered onto 2 ml of 0.225 g/ml metrizamide (density 1.120 g/ml) and centrifuged at room temperature for 15 min at 400×g. The cells remaining at the buffer-metrizamide interface were aspirated and discarded; the cells in the pellet were washed and resuspended in 1 ml of Tyrode buffer A containing calcium. Splenocytes were seeded into 24-well culture plates ($2 \times 10^5$ cells/well) in 0.4 ml medium for each well. Cells were incubated overnight at 37° C. and sensitized with 0.5 μg/ml of anti-$DNP_{24}$-BSA IgE. After sensitizing the cells with IgE, the medium was removed, and the cells were washed twice with 0.5 ml of PIPES buffer and preincubated with either 200 μl of PIPES buffer (as control), Cromolyn ($10^{-4}$ M) or hardy kiwifruit extract (100 μg/ml) at 37° C. for 10 min. Mast cells were stimulated with 20 ng/ml of $DNP_{24}$-BSA as an antigen for 30 min., and histamine released into the medium was measured by ELISA (ALerCHEK). Inhibition of histamine release was calculated as following empirical formula 1;

Percent inhibition=100×(A−B)/(A−C)   [Empirical Formula 1]

A: Stimulated level (Histamine release with IgE-stimulation).
B: Suppressed level (Histamine release with IgE-stimulation and drug treatment).
C: Basal level (Histamine release without IgE-stimulation).

Table 8 indicates that the hardy kiwifruit extract inhibited histamine release by approximately 44% at 100 μg/ml, and it was effective as much as Cromolyn used as a positive control.

TABLE 8

| Treatment | Cromolyn | Hardy kiwifruit |
|---|---|---|
| Inhibition (%) | 52 ± 13 | 44 ± 10 |

Experimental Example 6

Anti-Inflammatory Effects on Edema Induced by Arachidonic Acid in the Ears of Mice 15 mice (8 week old male BALB/c) were fasted for 18 hours with free access to water and divided into 3 groups. Inflammation was induced by topical application of arachidonic acid (0.5 mg/20 μl acetone) to the right ear of each mouse. The left ear was used as a negative control and received the vehicle (20 μl acetone). The hardy kiwifruit extract (200 mg/kg in water) was administered p.o. 1 hour prior to arachidonic acid application. The positive control group received indomethacin (10 mg/kg, p.o.) 1 hour before arachidonic acid application. Inflammation was followed for 1 hour and thereafter the animals were sacrificed. A section of 6 mm diameter disc from each ear was obtained and weighed. The edema index was assessed using the increase in the weight of the treated right ear punch biopsy over that of the untreated left ear. The edema index of the control mice that did not receive any treatment was 7.2±1.1 mg. However, when animals were treated with the hardy kiwifruit extract, the index was decreased by 62.5% to 2.7±0.8 mg. The ear treated with indomethacin as a positive control showed 81.9% decrease in edema index compared to the untreated ear (See Table 9).

This data suggested that the hardy kiwifruits had anti-inflammatory activity comparable to indomethacin in this experimental model.

TABLE 9

| Treatment | Index of edema | Inhibition rate (%) |
| --- | --- | --- |
| Control | 7.2 ± 1.1 | — |
| Hardy kiwifruit extract | 2.7 ± 0.8 | 62.5 |
| Indomethacin | 1.3 ± 0.3 | 81.9 |

Experimental Example 7

Experiment of Mouse Model with Allergic Dermatitis

To confirm anti-allergic effect of hardy kiwifruit extract in animals, Nc/Nga mouse model that has been widely used as an animal model for human atopic dermatitis study was employed. Nc/Nga mouse has suppressed Th1 immunity because of it's genetic character, i.e., low level of interferon-γ production and consequently, Th2 immunity becomes dominant, which predisposes Nc/Nga mouse to allergic disease, notably atopic dermatitis under normal circumstance (Vestergaar C H et al., *J. Clin. Invest.*, 104, pp 1097-1105, 1999).

For experiment, 15 of Nc/Nga mice (7 weeks after birth, female) were divided into 3 groups and adapted to new circumstance for 1 week. Since 8 weeks after birth, the hardy kiwifruit extract (300 μg/mouse/day) prepared in example 1-1 as a treatment group had been orally administered and dexamethasone (10 μg/mouse/day) or drinking water (100 μg/mouse/day) as control groups had been orally administered for 8 weeks. To compare the progress of dermatitis symptom, the scratching frequency of mouse (the time spent scratching during 20 min-observation) was measured when mice is grown at the age of 12 and 14 weeks. 16 weeks old mouse was sacrificed and the quantity of IgE, IgG1 and IgG2a level in serum were measured by ELISA method. Also, to compare the production of Th1/Th2 cytokines, splenocyte was prepared by conventional method from each mouse, transferred into 24-well plate ($5 \times 10^6$ cells/ml/well) and incubated with ConA (1 μg/ml) for 3 days and then the levels of IL-4, IL-5, IL-12, and Interferon-γ were measured by ELISA method.

Figure 2A:
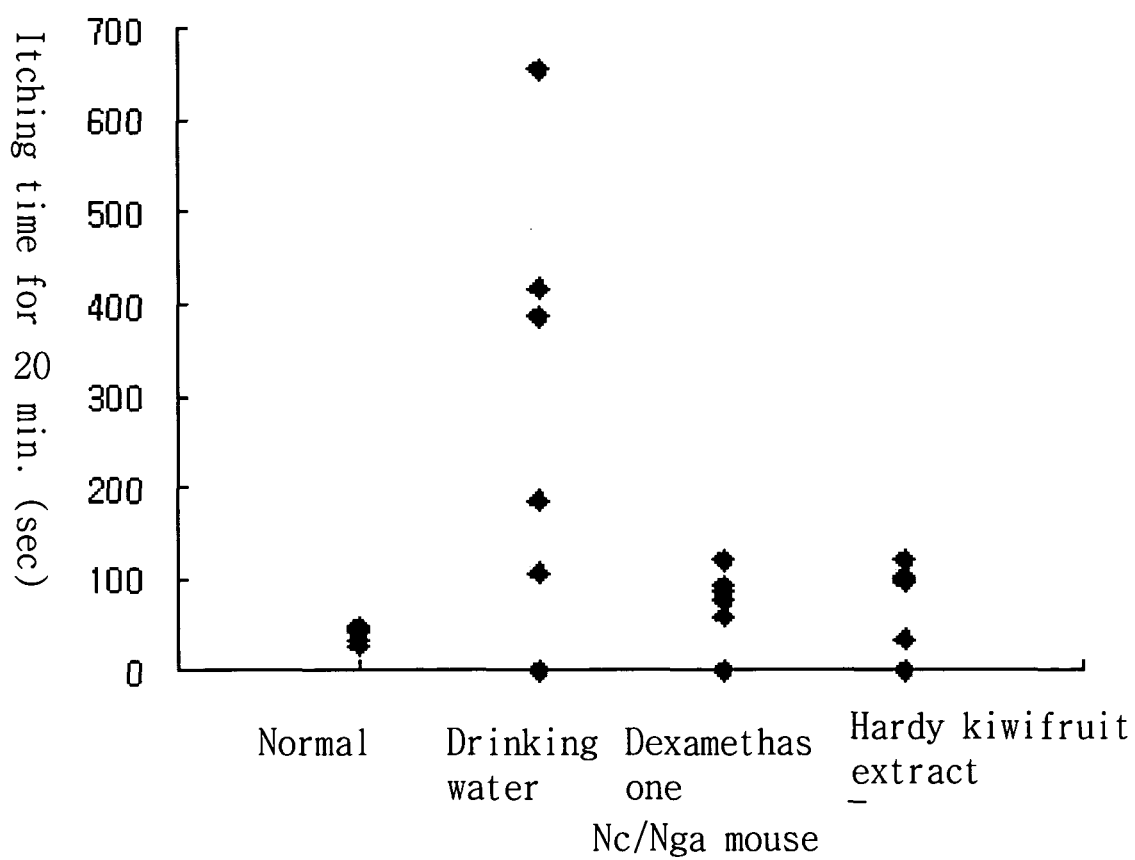
FIG. 2a presents result about symptom of skin itching, which investigated at the 12 weeks after administration the hardy kiwifruit extract in the Nc/Nga mouse having atopic dermatitis.
Figure 2B:
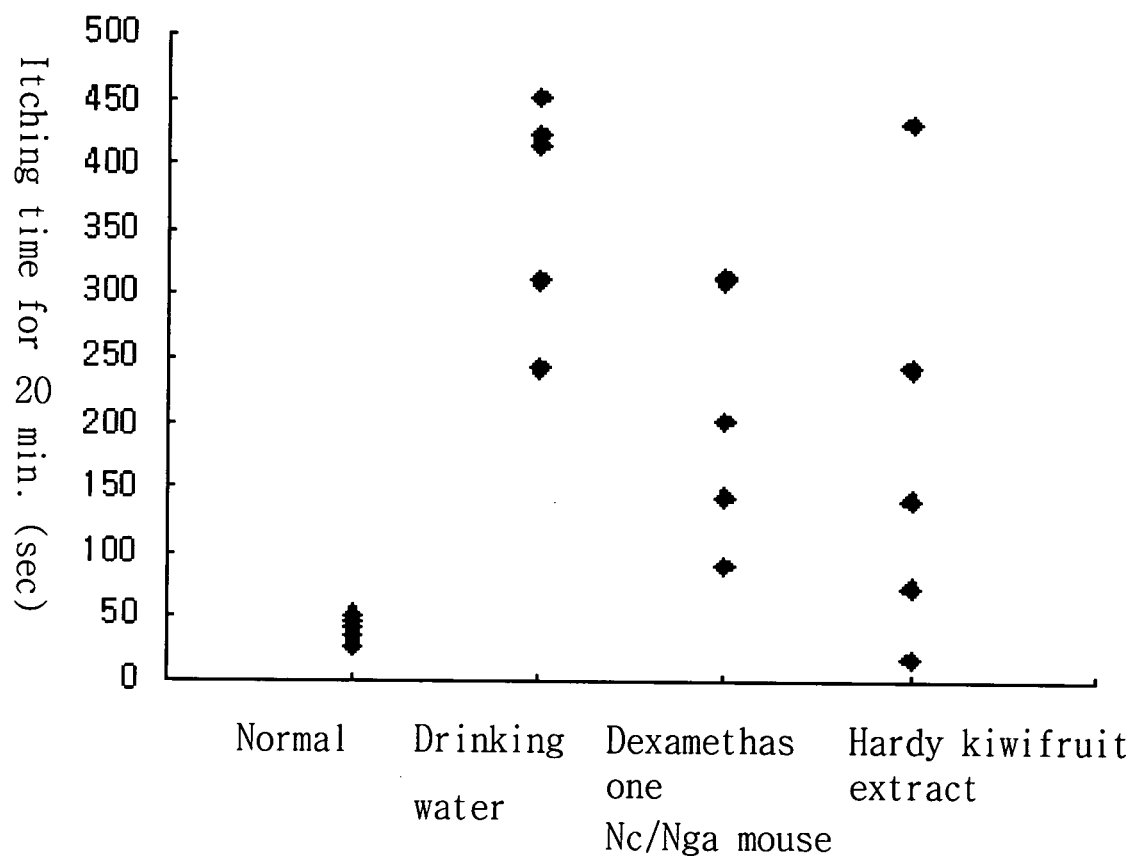
FIG. 2b presents result about symptom of skin itching, which investigated at the 14 weeks after administration the hardy kiwifruit extract in the Nc/Nga mouse having atopic dermatitis.

It was confirmed that the hardy kiwifruit extract repressed itching symptom as much as dexamethasone, a steroidal antiphlogistic agent, when the frequency of scratching was measured (See FIG. 2a: the result of 12 weeks after birth, FIG. 2b: the result of 14 weeks after birth).

Table 10 shows that the serum level of IgE of the hardy kiwifruit extract-administered mouse was reduced remarkably.

In the Table 11, the production of IL-4 and IL-5 was decreased and the production of interferon-γ and IL-12 was increased obviously in the splenocytes, which were prepared from the hardy kiwifruit extract-administered mouse. The hardy kiwifruit extract improved itching symptom, lowered IgE concentration in serum, and repressed the Th2 cytokine production by splenocytes (similarly with dexamethasone), but unlike dexamethasone, the hardy kiwifruit extract increased significantly IL-12 and interferon-γ level, which have been well known to contribute to alleviation of allergic diseases.

TABLE 10

| | IgE | IgG1 | IgG2a |
| --- | --- | --- | --- |
| Drinking water | 1572.9 ± 77.4 | 242.2 ± 14.2 | 177.5 ± 17.2 |
| Hardy kiwifruit extract | 699.0 ± 348.5 | 263.4 ± 21.1 | 263.5 ± 16.2 |
| Dexamethasone | 130.0 ± 55.3 | 247.3 ± 10.8 | 148.0 ± 14.8 | unit: pg/ml

TABLE 11

| | IL-4 | IL-5 | IL-12 | Interferon-γ |
| --- | --- | --- | --- | --- |
| Drinking water | 151.9 ± 2.2 | 778.3 ± 34.1 | 1925.7 ± 134.5 | 10407.5 ± 130.8 |
| Hardy kiwifruit extract | 24.1 ± 5.2 | 248.0 ± 17.8 | 2346.2 ± 98.4 | 15847.9 ± 1693.1 |
| Dexamethasone | 42.7 ± 19.4 | 646.5 ± 51.7 | 201.2 ± 12.1 | 10096.4 ± 192.4 | unit: pg/ml

Experimental Example 8

Toxicity Test

To examine the toxicity of the hardy kiwifruit extract, repetitive toxicity tests were performed on mouse.

The 10 female of Balb/c mice were divided into 2 groups and the inventive hardy kiwifruit extract (150 mg/kg) was administered to the mice at 150 mg/kg for 4 weeks and water was administered to the control group. The symptom of toxicity was observed for 4 weeks such as the change of weight, the hematological analysis and histological test.

As a result of experiment, there was no death example of the mice administered with 150 mg/kg inventive hardy kiwifruit and there was no significant abnormality in the gain of weight, the caloric intake of feed, the hematological analysis or the histological test etc. In accordance with above results, it was confirmed that the hardy kiwifruit was safe.

(1) Weight and behavior observation: the unusual change of weight or behavior was not observed.
(2) Hematological analysis: No abnormal symptom was observed in the number of WBC, lymphocyte, monocyte, neutrophil, eosinophil, basophil, RBC, hemoglobin or platelet.
(3) Serum biochemical test: No abnormal symptom was observed in the level of AST, ALT, LDH, bilirubin, creatinine, glucose, cholesterol, minerals, albumin, BUN, lipase or amylase of serum.
(4) Histological test: No abnormal symptom was observed in the tissue of kidneys, the spleen, the liver or the thymus.

Hereinafter, the formulating methods and kinds of excipients will be described, but the present invention is not limited to them. The representative preparation examples were described as follows.

| Preparation of injection | |
| --- | --- |
| Hardy kiwifruit water extract of Example 1 | 50 mg |
| Sodium metadisulfite | 3.0 mg |
| Methylparaben | 0.8 mg |
| Propylparaben | 0.1 mg |
| Distilled water for injection | optimum amount |

Injection preparation was prepared by mixing above components and making 2 ml by the conventional method and then filing filling all the components 2 ml ample and sterilizing by conventional injection preparation method.

| Preparation of tablet | |
| --- | --- |
| Hardy kiwifruit water extract of Example 1 | 50 mg |
| Corn Starch | 100 mg |
| Lactose | 100 mg |
| Magnesium Stearate | 2 mg |

Tablet preparation was prepared by mixing above components and entabletting.

| Preparation of capsule | |
| --- | --- |
| Hardy kiwifruit water extract of Example 1 | 100 mg |
| Corn starch | 100 mg |
| Lactose | 100 mg |
| Talc | 2 mg |
| Magnesium Stearate | optimum amount |

Tablet preparation was prepared by mixing above components and filling gelatin capsule by conventional gelatin preparation method.

| Preparation of liquid | |
| --- | --- |
| The hardy kiwifruit 70% ethanol extract | 100 mg |
| Sugar | 20 g |
| Fructose | 20 g |
| Lemon flavour | optimum amount |
| Distilled water | 100 ml |

Liquid preparation was prepared by mixing above components and then filling 100 ml brown bottle sterilizing by conventional liquid preparation method.

| Preparation of health care food | |
| --- | --- |
| Hardy kiwifruit water extract of Example 1 | 1000 mg |
| Vitamin mixture | 20 g |
| Vitamin A acetate | 70 μg |
| Vitamin E | 1.0 mg |
| Vitamin $B_1$ | 0.13 mg |
| Vitamin $B_2$ | 0.15 mg |
| Vitamin B6 | 0.5 mg |
| Vitamin B12 | 0.2 μg |
| Vitamin C | 10 mg |
| Biotin | 10 μg |
| Amide nicotinic acid | 1.7 mg |
| Folic acid | 50 μg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |

| Preparation of health care food | |
| --- | --- |
| Calcium carbonates | 100 mg |
| Magnesium chloride | 24.8 mg |

The above-mentioned vitamin and mineral mixture may be varied in many ways. Such variations are not to be regarded as a departure from the spirit and scope of the present invention.

| Preparation of health beverage | |
| --- | --- |
| Hardy kiwifruit water extract of Example 1 | 1000 mg |
| Citric acid | 100 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 2000 ml ample and sterilizing by conventional health beverage preparation method.

| Preparation of skin lotion | |
| --- | --- |
| Hardy kiwifruit water extract of Example 1 | 1.00(%) |
| Glycerol | 3.00 |
| Ethanol | 1.00 |
| Propylene glycol | 0.10 |
| Flavour | trace amount |
| Distilled water | made to 100% |

Skin preparation was prepared by dissolving active component according to conventional lotion preparation method.

| Preparation of lotion | |
| --- | --- |
| Hardy kiwifruit water extract of Example 1 | 3.00(%) |
| L-ascorbic acid-2-magnesium phosphate | 1.00 |
| Soluble collagen (1% solution) | 1.00 |
| Sodium citric acid | 0.10 |
| Citric acid | 0.05 |
| 1,3-butylene glycol | 3.00 |
| Distilled water | made to 100% |

Lotion preparation was prepared by dissolving active component according to conventional lotion preparation method.

| Preparation of cream | |
| --- | --- |
| Hardy kiwifruit water extract of Example 1 | 3.00(%) |
| Polyethyleneglycomonosterate | 2.00 |
| Monostearate glycerin | 1.00 |
| Cetyl alcohol | 4.00 |
| Squalene | 6.00 |
| Tri 2-glyceryl ethylhexanoate | 6.00 |
| Sphingo-glycolipid | 1.00 |
| 1,3-butylene glycol | 7.00 |
| Distilled water | made to 100% |

| Preparation of pack | |
| --- | --- |
| Hardy kiwifruit water extract of Example 1 | 5.00(%) |
| Polyvinyl alcohol | 13.00 |
| L-ascorbic acid-2-magnesium phosphate | 1.00 |
| Lauroylhydroxyproline | 1.00 |
| Soluble collagen (1% solution) | 2.00 |
| 1,3-butylene glycol | 3.00 |
| Ethanol | 5.00 |
| Distilled water | made to 100% |

Pack preparation was prepared by dissolving active component according to conventional pack preparation method.

| Preparation of beauty solution | |
| --- | --- |
| Hardy kiwifruit water extract of Example 1 | 2.00(%) |
| Hydroxyethylenecellulose (2% solution) | 12.00 |
| Xanthin gum (2% solution) | 2.00 |
| 1,3-butylene glycol | 3.00 |
| Conc. Glycerin | 4.00 |
| Sodium hyaluronate | 5.00 |
| Distilled water | made to 100% |

Beauty solution preparation was prepared by dissolving active component according to conventional beauty solution preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, an extract of the hardy kiwifruit extract prepared by inventive preparation increase serum levels of Th1 cytokines and IgG2a, reduce serum levels of Th2 cytokines and IgE, inhibits histamine release from mast cells, and suppresses inflammatory reaction. According to this, the hardy kiwifruit can be used as a pharmaceutical composition for the treatment and prevention of allergic diseases, such as anaphylaxis, allergic rhinitis, asthma, atopic dermatitis, food allergies and urticaria and non-allergic inflammation disease.

Furthermore, an extract of the hardy kiwifruit extract can be used as a composition of healthy food for the treatment and prevention of allergic diseases, such as anaphylaxis, allergic rhinitis, asthma, atopic dermatitis, food allergies and urticaria and non-allergic inflammation disease.

What is claimed is:

1. A method for simultaneously decreasing Th2 serum cytokines and increasing Th1 serum cytokines in a mammal in need thereof, said method comprising orally administering an extract of *Actinidia arguta* to said mammal, wherein said extract is provided in an amount sufficient to simultaneously decrease serum Th2 cytokines and increase serum Th1 cytokines in said mammal.

2. The method of claim 1, wherein the extract is prepared from a part of *Actinidia arguta* selected from the group consisting of: the fruit, the stem, the root, and any combination thereof.

3. The method of claim 1, wherein the extract is selected from the group consisting of a crude extract and a non-polar solvent soluble extract.

4. The method of claim 3, wherein the crude extract is soluble in a polar solvent selected from the group consisting of: distilled water, lower alcohols, and mixtures thereof.

5. The method of claim 3, wherein the crude extract is soluble in distilled water or 70% ethanol.

6. The method of claim 3, wherein the non-polar solvent is ethyl acetate.

7. The method of claim 1, wherein the extract is provided in a composition in an amount of between about 0.01% and about 30% by weight based on the total weight of the composition.

8. The method of claim 1, wherein the extract is provided in a composition in an amount of between 0.01% and about 50% by weight based on the total weight of the composition.

9. The method of claim 1, wherein the extract is provided in a composition in an amount of between about 0.01% and about 80% by weight based on the total weight of the composition.

10. The method of claim 1, wherein the Th2 cytokines are selected from the group consisting of: interleukin-4 (IL-4), IL-5 and IL-13.

11. The method of claim 10, wherein the Th2 cytokines comprise IL-4, IL-5 and IL-13.

12. The method of claim 1, wherein the Th1 cytokines comprise interferon-$\gamma$.

* * * * *